United States Patent
Gonenc et al.

(10) Patent No.: US 12,369,938 B2
(45) Date of Patent: Jul. 29, 2025

(54) METHOD AND SYSTEM FOR MODEL-BASED TEMPERATURE ESTIMATION OF AN ULTRASONIC INSTRUMENT

(71) Applicant: Verb Surgical Inc., Santa Clara, CA (US)

(72) Inventors: Berk Gonenc, San Jose, CA (US); Amirhossein Farvardin, San Jose, CA (US); Steven Boronyak, Cincinnati, OH (US); Sean Conlon, Loveland, OH (US)

(73) Assignee: Verb Surgical Inc., Santa Clara, CA (US)

( * ) Notice: Subject to any disclaimer, the term of this patent is extended or adjusted under 35 U.S.C. 154(b) by 670 days.

(21) Appl. No.: 17/723,412

(22) Filed: Apr. 18, 2022

(65) Prior Publication Data
US 2023/0329743 A1  Oct. 19, 2023

(51) Int. Cl.
*A61B 17/32*  (2006.01)
*A61B 17/00*  (2006.01)

(52) U.S. Cl.
CPC ........... *A61B 17/320092* (2013.01); *A61B 17/320016* (2013.01); *A61B 2017/00084* (2013.01);
(Continued)

(58) Field of Classification Search
CPC .... A61B 17/320016; A61B 17/320092; A61B 2017/00084; A61B 2017/00106;
(Continued)

(56) References Cited

U.S. PATENT DOCUMENTS 10,405,914 B2   9/2019  Manwaring et al.
10,955,387 B2   3/2021  Ross et al.
(Continued)

FOREIGN PATENT DOCUMENTS

KR   20190061586 A   6/2019
KR   20210064750 A   6/2021
WO   2021110847 A2   6/2021

OTHER PUBLICATIONS

PCT/IB2023/053101, "PCT International Search Report and Written Opinion of the International Searching Authority", mailed Jul. 13, 2023, 11 pages.
(Continued)

*Primary Examiner* — Tigist S Demie
(74) *Attorney, Agent, or Firm* — Aikin & Gallant, LLP

(57) ABSTRACT

A method performed by a surgical system that includes an ultrasonic instrument with an end effector. The method determines a change in resonance frequency of the end effector while the ultrasonic instrument is either in 1) a high-power state in which the ultrasonic instrument draws a first current to cause the end effector to produce heat or 2) a low-power state in which the ultrasonic instrument draws a second current, which is less than the first current that does not cause the end effector to produce heat. The method determines a temperature of the end effector by applying the change in resonance frequency to a hysteresis model that includes a hysteretic relationship between changes in resonance frequency of the end effector and corresponding temperatures of the end effector, and outputs a notification based on the temperature.

20 Claims, 12 Drawing Sheets

(52) U.S. Cl.
CPC ............... *A61B 2017/00106* (2013.01); *A61B 2017/00115* (2013.01); *A61B 2017/320093* (2017.08); *A61B 2017/320095* (2017.08)

(58) Field of Classification Search
CPC ......... A61B 2017/00115; A61B 2017/320093; A61B 2017/320095
See application file for complete search history.

(56) References Cited

U.S. PATENT DOCUMENTS

| | | | |
|---|---|---|---|
| 2013/0331874 A1* | 12/2013 | Ross | G01N 29/44 |
| | | | 702/19 |
| 2021/0153889 A1* | 5/2021 | Nott | A61B 5/068 |
| 2023/0007851 A1* | 1/2023 | Hancock | A61B 18/1815 |

OTHER PUBLICATIONS

Kim et al., "Everett Function Formulation Using Minor Loops and Magnetization-dependent Model and Hysteresis Characteristics Simulation", received from https://koreascience.kr/article/JAKO201707464562672.view?orgId=anpor, Published : Dec. 1, 2017, 7 pages.

* cited by examiner

METHOD AND SYSTEM FOR MODEL-BASED TEMPERATURE ESTIMATION OF AN ULTRASONIC INSTRUMENT

FIELD

Various aspects of the disclosure relate generally to surgical systems that estimates temperature of an ultrasonic instrument using a temperature model, while the instrument is in use during a surgical procedure. Other aspects are also described.

BACKGROUND

Minimally-invasive surgery, MIS, such as laparoscopic surgery, uses techniques that are intended to reduce tissue damage during a surgical procedure. Laparoscopic procedures typically call for creating a number of small incisions in the patient, e.g., in the abdomen, through which several surgical tools such as an endoscope, a blade, a grasper, and a needle, are then inserted into the patient. A gas is injected into the abdomen which insufflates the abdomen thereby providing more space around the tips of the tools, making it easier for the surgeon to see (via the endoscope) and manipulate tissue at the surgical site. MIS can be performed faster and with less surgeon fatigue using a surgical robotic system in which the surgical tools are operatively attached to the distal ends of robotic arms, and a control system actuates the arm and its attached tool. The tip of the tool will mimic the position and orientation movements of a handheld user input device (UID) as the latter is being manipulated by the surgeon. The surgical robotic system may have multiple surgical arms, one or more of which has an attached endoscope and others have attached surgical instruments for performing certain surgical actions.

Control inputs from a user (e.g., surgeon or other operator) are captured via one or more user input devices and then translated into control of the robotic system. For example, in response to user commands, a tool drive having one or more motors may actuate one or more degrees of freedom of a surgical tool when the surgical tool is positioned at the surgical site in the patient.

SUMMARY

A surgical tool that is used in some MIS procedures is an ultrasonic instrument that uses ultrasonic vibration at its tip to rapidly generate heat for cutting and cauterizing tissue. The tip may include a blade that reaches high temperatures (e.g., greater than 300° C.) during a "heating" cycle in which the blade oscillates against a piece of tissue, thereby producing heat due to friction between the blade and the tissue during the oscillation. After reaching a high temperature, the blade may be used to dissect a portion of the tissue, while also sealing the remaining tissue. By performing multiple tasks (e.g., cutting for dissection, cauterizing, etc.), the use of the tool during a laparoscopic surgery reduces instrument exchanges and the number of instruments during the procedure.

An ultrasonic instrument may be repeatedly activated by an operator of a laparoscopic surgical system in order to perform several surgical tasks, such as cuts and/or long tissue seals. After a sealing or cutting task is finished, the blade of the instrument may be deactivated and enter a "cooling cycle", in which the blade begins to cool down from the high temperature at which the blade was used to perform the surgical task. At the beginning of the cooling cycle, the blade may still be hot due to residual heat on the blade. This heat may take a while (e.g., a significant period of time) to dissipate. As a result, while the instrument is in the cooling cycle, the operator must take care to avoid touching remaining tissue in order to avoid inadvertently causing thermal injuries to potentially sensitive tissue. There is currently, however, no mechanism to notify operators of laparoscopic surgical systems what the temperature at the blade is, and therefore, they must rely on their experience to guess when the blade is cooled down enough to continue manipulating other tissues without causing thermal damage. In the case of repeated activation/deactivation (e.g., repeatedly transitioning between heating and cooling cycles) for performing different types of surgical tasks (e.g., longer/shorter seals and/or cuts), it becomes even more challenging for an operator to manually tell (or estimate) the temperature of the blade and when it has sufficiently cooled. Therefore, there is a need for estimating (or determining) temperature information of ultrasonic instruments for notifying operators of the instrument's (current or real-time) temperature status.

The present disclosure provides a surgical system that estimates (or determines) a temperature of an ultrasonic instrument, while the instrument is being used by an operator and outputs a notification that may include the estimated temperature. The system determines a change in resonance frequency of the end effector while the ultrasonic instrument is either in a "high-power" state (e.g., a heating cycle) in which the ultrasonic instrument draws a first current to cause the end effector to produce (e.g., frictional) heat or 2) a "low-current" state (e.g., a cooling cycle) in which the ultrasonic instrument draws a second current, which is less than the first current, that does not cause the end effector to produce heat. The system determines a temperature of the end effector by applying the change in resonance frequency to a temperature (e.g., hysteresis) model that includes a hysteretic relationship between changes in resonance frequency of an end effector (e.g., that includes a blade) of the ultrasonic instrument and corresponding temperatures of the end effector. In one aspect, the model may have been previously defined in a controlled environment (e.g., in a laboratory). In some aspects, the temperature may be output of the model when the change in frequency is input into the model. The system outputs a notification based on the temperature. For instance, the system may display a (e.g., pop-up) notification that includes the temperature.

In one aspect, the hysteresis model includes one or more hysteresis loops, each loop having a first temperature curve that has a first set of temperatures with respect to several changes in resonance frequency and a second temperature curve that has a second set of temperatures with respect to the several changes in resonance frequencies. In particular, each hysteresis loop includes two (e.g., different) temperatures for change in resonance frequency. For example, each change in resonance frequency may be associated with a respective temperature of the second set and another respective temperature of the first set that is greater than the respective temperature of the second set. This may due to the first temperature curve being associate with temperature values of the end effector that increase with respect to increasing changes in resonance frequency, and the second temperature curve being associated with temperature values of the end effector that decrease with respect to decreasing changes in resonance frequencies. In one aspect, the first temperature curve may be used to identify the temperature that corresponds to the determined change in resonance frequency, while the ultrasonic instrument is in the high-power state, and the second temperature curve may be used to identify the temperature that corresponds to the determined change in resonance frequency, while the ultrasonic instrument is in the low-power state.

In one aspect, the end effector may include a blade that vibrates along a longitudinal axis and may include a hinged arm that is rotatably coupled about a transverse axis to a joint of the end effector. In some aspects, the blade vibrates (e.g., reciprocating back and forth) 1) over a first excursion (e.g., the blade moving forward (or backward) from a starting position by a first distance) while the ultrasonic instrument is in the high-power state to produce the heat and 2) over a second excursion that is less than the first excursion below the frequency threshold while the ultrasonic instrument is in the low-power state.

In some aspects, the surgical system may perform one or more operations based on the determined temperature. For example, the system may determine a desired temperature range for the end effector, and may maintain the temperature of the end effector within the desired temperature range by controlling whether the ultrasonic instrument is in the high-power state or the low-power state based on one or more (e.g., future) changes in resonance frequency of the end effector. In another aspect, the system determines whether the temperature is less than a temperature threshold, and in response to determining that the temperature is less than the temperature threshold, ceases to output the notification. For example, the notification may be displayed on a display of the surgical system, and may indicate that the end effector is hot (e.g., reading "End Effector is Hot!"). As another example, the notification may be an audible alert that is played back by a speaker of the surgical system. In particular, the surgical system may drive speaker 43 with an audio signal that includes the audible alert that relates to the temperature (e.g., playing back a currently determined temperature, etc.). Once the temperature has dropped below the threshold, this may mean that the end effector has sufficiently cooled down. As a result, the system may cease to output the notification, which may alert the operator of the system that the ultrasonic instrument is no longer hot.

According to another aspect of the disclosure, the surgical system may be configured to perform closed-loop temperature control of the ultrasonic instrument. In particular, the system determines a change in resonance frequency of a blade of the instrument's end effector. The system determines a temperature of the blade by applying the change in resonance frequency as input into a hysteresis model that produces the temperature as output. The system maintains a desired temperature range of the blade by switching between a high-power state in which the ultrasonic instrument draws a first current to cause the blade to produce heat and a low-power state in which the ultrasonic instrument draws a second current that is less than the first current and does not cause the blade to produce heat, based on the determined temperature.

In one aspect, the change in resonance frequency is determined while the ultrasonic instrument is used by an operator during a surgical procedure and is operating in either the high-power state or the low-power state. In another aspect, maintaining the desired temperature range includes, in response to determining that the determined temperature is inside or greater than the desired temperature range, operating in the low-power state and, in response to determining that the determined temperature is less than the desired temperature range, operating in the high-power state. In some aspects, the system determines the desired temperature range via an input device (e.g., a touch-sensitive display screen, etc.) that is communicatively coupled to the surgical system. In another aspect, the desired temperature range is a particular user-desired temperature.

In some aspects, the system receives endoscopic video of a surgical site, performs an image recognition algorithm upon the endoscopic video to identify a piece of tissue in the surgical site upon which a surgical task is to be performed by the ultrasonic instrument, and determine the desired temperature range of the blade based on the piece of tissue. In another aspect, the desired temperature range is maintained without user a temperature sensor.

According to another aspect of the disclosure, the surgical system may be configured to create a hysteresis model, which may be used (e.g., in real-time) to estimate the temperature of the end effector while the ultrasonic instrument is being used by an operator. The system experimentally determines a first set of temperature data with respect to changes in resonance frequency of the end effector of the ultrasonic instrument that is configured to operate in either 1) a high-power state in which the ultrasonic instrument draws power for the end effector to produce heat or 2) a low-power state in which the ultrasonic instrument draws less power that does not cause the end effector to produce heat. The system uses the first set of temperature data to determine additional temperature data with respect to changes in resonance frequency of the end effector as a second set of temperature data. For example, this additional temperature data may be determined using one or more methods, such as interpolation or a polynomial fit approach. The system generates the hysteresis model that includes (or defines) a hysteretic relationship between changes in resonance frequency and temperatures of the end effector using the first and second sets of temperature data.

The above summary does not include an exhaustive list of all aspects of the disclosure. It is contemplated that the disclosure includes all systems and methods that can be practiced from all suitable combinations of the various aspects summarized above, as well as those disclosed in the Detailed Description below and particularly pointed out in the claims. Such combinations may have particular advantages not specifically recited in the above summary.

BRIEF DESCRIPTION OF THE DRAWINGS

The aspects are illustrated by way of example and not by way of limitation in the figures of the accompanying drawings in which like references indicate similar elements. It should be noted that references to "an" or "one" aspect of this disclosure are not necessarily to the same aspect, and they mean at least one. Also, in the interest of conciseness and reducing the total number of figures, a given figure may be used to illustrate the features of more than one aspect, and not all elements in the figure may be required for a given aspect.

DETAILED DESCRIPTION

Several aspects of the disclosure with reference to the appended drawings are now explained. Whenever the shapes, relative positions and other aspects of the parts described in a given aspect are not explicitly defined, the scope of the disclosure here is not limited only to the parts shown, which are meant merely for the purpose of illustration. Also, while numerous details are set forth, it is understood that some aspects may be practiced without these details. In other instances, well-known circuits, structures, and techniques have not been shown in detail so as not to obscure the understanding of this description. Furthermore, unless the meaning is clearly to the contrary, all ranges set forth herein are deemed to be inclusive of each range's endpoints.

Figure 1:
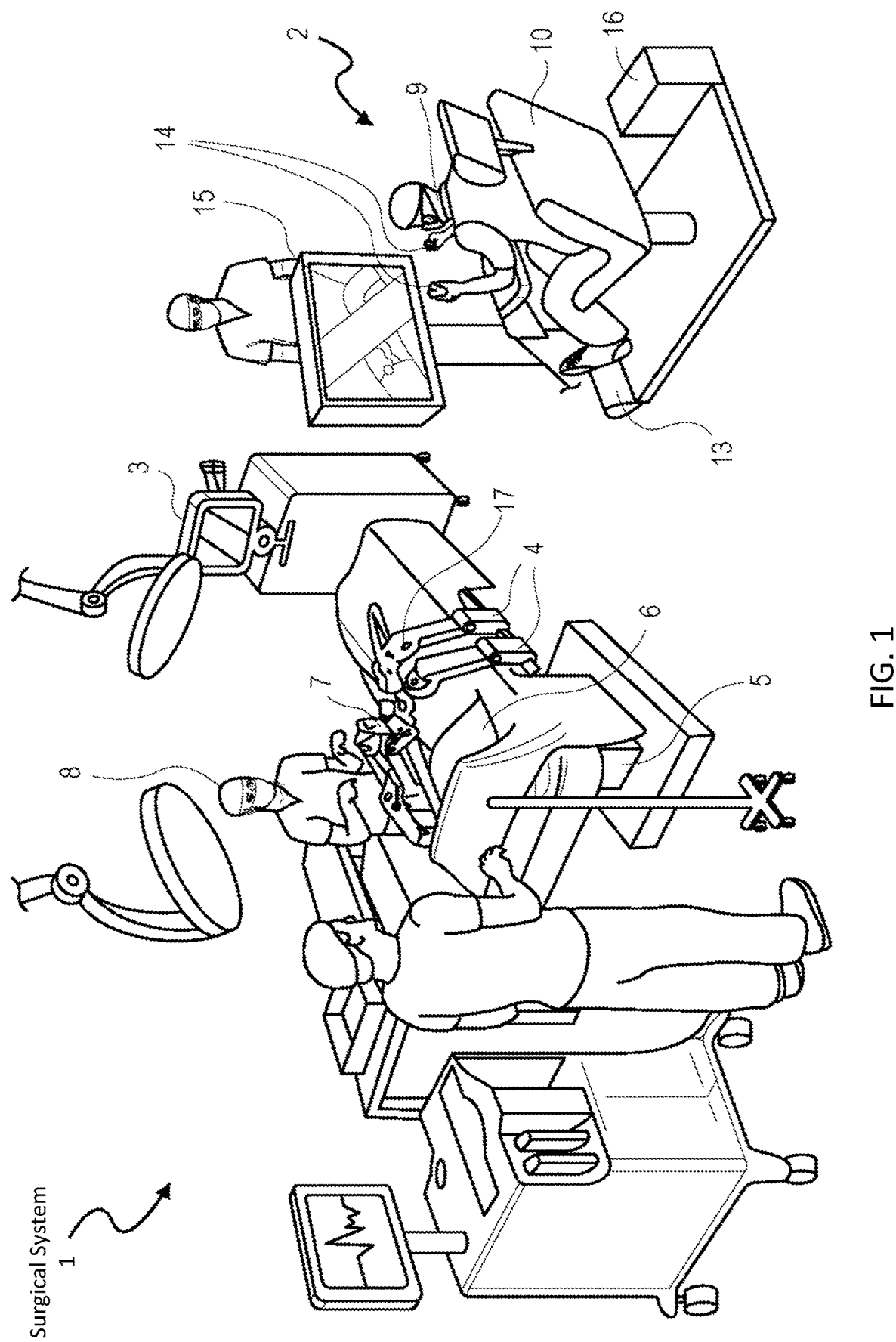
FIG. 1 shows a pictorial view of an example surgical system in an operating arena.

FIG. 1 shows a pictorial view of an example surgical system (which hereafter may be referred to as "system") 1 in an operating arena. The system 1 includes a user console 2, a control tower 3, and one or more surgical robotic arms 4 at a surgical robotic table (surgical table or surgical platform) 5. In one aspect, the arms 4 may be mounted to a table or bed on which the patient rests as shown in the example of FIG. 1. In one aspect, at least some of the arms 4 may be configured differently. For example, at least some of the arms may be mounted on a ceiling, sidewall, or in another suitable structural support, such as a cart separate from the table. The system 1 can incorporate any number of devices, tools, or accessories used to perform surgery on a patient 6. For example, the system 1 may include one or more surgical tools (instruments) 7 used to perform surgery (surgical procedure). A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an aspect, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. For example, when manually controlled an operator may (e.g., physically) hold a portion of the tool (e.g., a handle), and may manually control the tool by moving the handle and/or pressing one or more input controls (e.g., buttons) on the (e.g., handle of the) tool. In another aspect, when controlled robotically, the surgical system may manipulate the surgical tool based user input (e.g., received via the user console 2, as described herein).

Generally, a remote operator 9, such as a surgeon or other operator, may use the user console 2 to remotely manipulate the arms 4 and/or the attached surgical tools 7, e.g., during a teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may include one or more components, such as a seat 10, one or more foot-operated controls (or foot pedals) 13, one or more (handheld) user-input devices (UIDs) 14, and at least one display 15. The display is configured to display, for example, a view of the surgical site inside the patient 6. The display may be configured to display image data (e.g., still images and/or video). In one aspect, the display may be any type of display, such as a liquid crystal display (LCD), a light-emitting diode (LED) display, an organic LED (OLED) display, etc. In some aspects, the display may be a 3D immersive display that is for displaying 3D (surgical) presentations. For instance, during a surgical procedure one or more endoscopic cameras may be capturing image data of a surgical site, which the display presents to the user in 3D. In one aspect, the 3D display may be an autostereoscopic display that provides 3D perception to the user without the need for special glasses. As another example, the 3D display may be a stereoscopic display that provides 3D perception with the use of glasses (e.g., via active shutter or polarized).

In another aspect, the display 15 may be configured to display at last one graphical user interface (GUI) that may provide informative and/or interactive content, to thereby assist a user in performing a surgical procedure with one or more instruments in the surgical system 1. For example, some of the content displayed may include image data captured by one or more endoscopic cameras, as described herein. In another aspect, the GUI may include selectable UI items, which when manipulated by the user may cause the system to perform one or more operations. For instance, the GUI may include a UI item as interactive content to switch control between robotic arms. In one aspect, to interact with the GUI, the system may include input devices, such as a keyboard, a mouse, etc. In another aspect, the user may interact with the GUI using the UID 14. For instance, the user may manipulate the UID to navigate through the GUI, (e.g., with a cursor), and to make a selection may hover the cursor over a UI item and manipulate the UID (e.g., selecting a control or button). In some aspects, the display may be a touch-sensitive display screen. In this case, the user may perform a selection by navigating and selecting through touching the display. In some aspects, any method may be used to navigate and/or select a UI item.

As shown, the remote operator 9 is sitting in the seat 10 and viewing the user display 15 while manipulating a foot-operated control 13 and a handheld UID 14 in order to remotely control one or more of the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the system 1 are in a stowed configuration or withdrawn configuration (to facilitate access to the surgical site.) Once access is completed, initial positioning or preparation of the system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one aspect, the remote operator 9 holds and moves the UID 14 to provide an input command to drive (move) one or more robotic arm actuators 17 (or driving mechanism) in the system 1 for teleoperation. The UID 14 may be communicatively coupled to the rest of the system 1, e.g., via a console computer system 16 (or host). The UID 14 can generate spatial state signals corresponding to movement of the UID 14, e.g. position and orientation of the handheld housing of the UID, and the spatial state signals may be input signals to control motions of the robotic arm actuators 17. The system 1 may use control signals derived from the spatial state signals, to control proportional motion of the actuators 17. In one aspect, a console processor of the console computer system 16 receives the spatial state signals and generates the corresponding control signals. Based on these control signals, which control how the actuators 17 are energized to drive a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn drives other linkages, gears, etc., of the system 1. The system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator that opens or closes jaws of the grasper at a distal end of surgical tool 7 to grip tissue within patient 6.

In some aspects, the communication between the surgical robotic table 5 and the user console 2 may be through a control tower 3, which may translate user commands that are received from the user console 2 (and more particularly from the console computer system 16) into robotic control commands that transmitted to the arms 4 on the surgical table 5. The control tower 3 may also transmit status and feedback from the surgical table 5 back to the user console 2. The communication connections between the surgical table 5, the user console 2, and the control tower 3 may be via wired (e.g., optical fiber) and/or wireless links, using any suitable one of a variety of wireless data communication protocols, such as BLUETOOTH protocol. Any wired connections may be optionally built into the floor and/or walls or ceiling of the operating room. The system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 2:
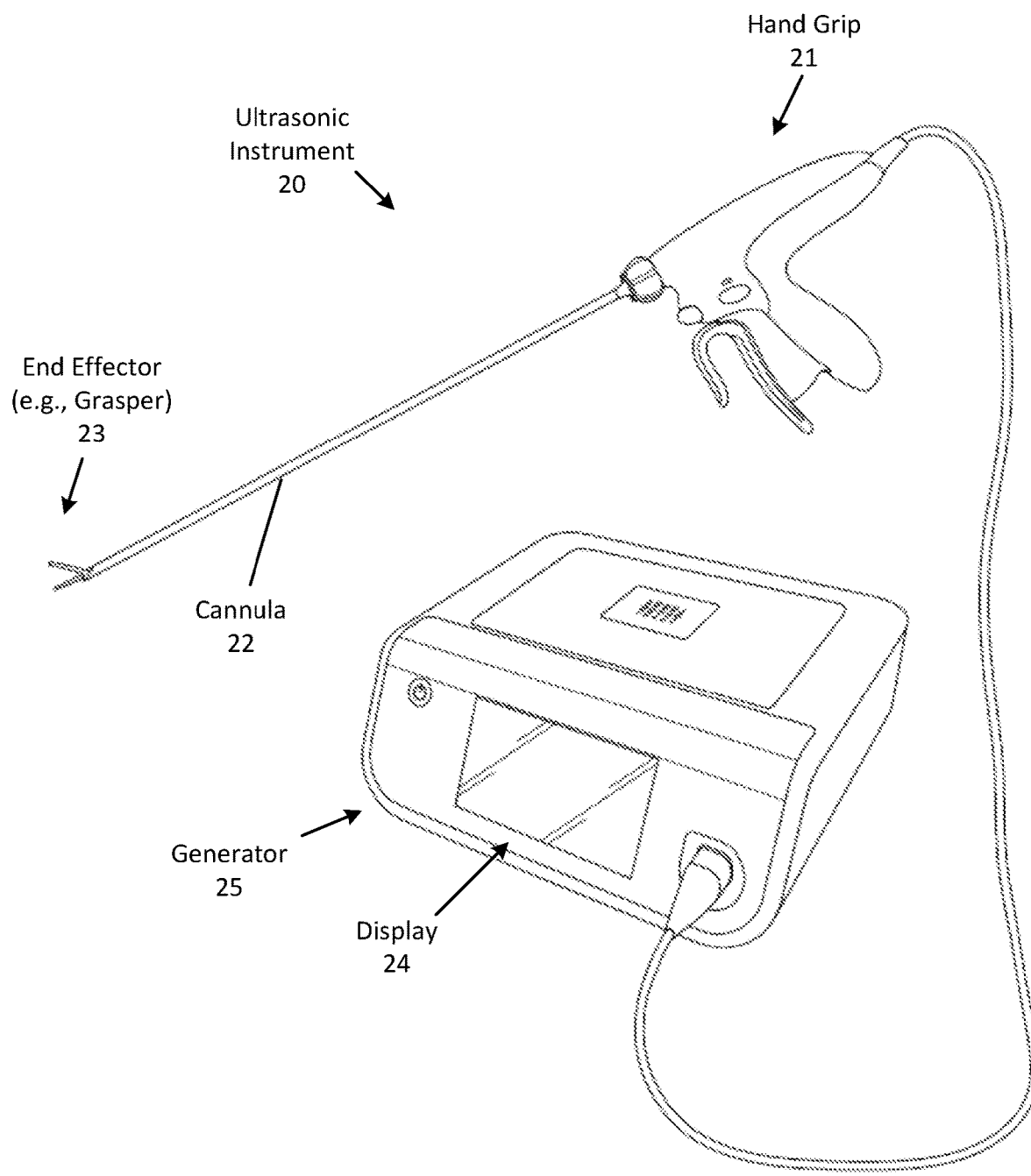
FIG. 2 shows a pictorial view of an ultrasonic instrument and a generator according to one aspect of the disclosure.

FIG. 2 shows a pictorial view of an ultrasonic instrument 20 and a generator 25 according to one aspect of the disclosure. As shown, the ultrasonic instrument is a handheld laparoscopic tool that is configured to perform ultrasonic surgical operations (e.g., cutting and sealing tissue) based on manual operations (e.g., of the hand grip 21) of the instrument by an operator (e.g., surgeon). The ultrasonic instrument is coupled (e.g., via a cable) to the generator that enables the ultrasonic instrument to operate in one or more power states, as described herein.

The ultrasonic instrument includes a hand grip (e.g., which includes a tool drive) 21, a cannula 22, and an end effector 23 (e.g., which may be coupled to a shaft of the instrument) that is loaded into the cannula, in accordance with aspects of the subject technology.

The hand grip 21 is arranged to be held by an operator, and allows the operator to manipulate the (e.g., end effector 23 of the) ultrasonic instrument during a surgical operation. In one embodiment, the hand grip may include one or more inputs (e.g., a trigger, one or more buttons, etc.), that allow an operator to control the ultrasonic instrument. For example, the instrument may include a trigger that produces a control signal in response to user input by pulling the trigger with one or more fingers while holding the hand grip. In one embodiment, the trigger may be arranged to manipulate the end effector (e.g., by adjusting the position of the hinged arm 31 shown in FIG. 3). In another embodiment, the hand grip may include one or more inputs for changing the power state of the instrument.

As described herein, the hand grip may include a tool drive that is arranged to drive the end effector 23 of the ultrasonic instrument. Specifically, the tool drive may include a (e.g., linear) motor or actuator that is arranged to vibrate (or oscillate) the end effector at one or more frequencies (e.g., at a very high (ultrasonic) frequency, and at a low frequency). In some aspects, the tool drive is configured to vibrate the end effector such that a portion of the end effector (e.g., a blade) moves back and forth along one or more axes. Specifically, the tool drive may vibrate the end effector over one or more excursions, where over each excursion the end effector may be displaced at a different distance from a starting (or beginning) position. More about how the end effector vibrates is described herein. In another aspect, the tool drive may include an ultrasonic transducer that is configured to vibrate the end effector according to an input voltage/input current (e.g., applied by the generator 25).

As described thus far, the ultrasonic instrument may include the end effector 23 and the tool drive 21. In one aspect, the ultrasonic instrument may be separate from (and removeably coupled to) the tool drive. In which case, the ultrasonic instrument as referred herein may be the end effector, which may be coupled to the (e.g., tool drive via the cannula of the) hand grip. Specifically, the cannula may be coupled to the hand grip, where the cannula receives and guides (e.g., a shaft of) the ultrasonic instrument in order to couple to the instrument. By being separate from the hand grip, this may allow multiple different tools to be coupled to the hand grip. In this case, the cannula 22 may receive and guide one or more surgical instruments, such as endoscopes, staplers, etc.

As described herein, the surgical system 1 includes the ultrasonic instrument 20 that is configured to produce heat based on vibrations of its end effector 23. In another embodiment, the instrument may be any type of energy (e.g., laparoscopic) tool that is designed to generate heat.

As described thus far, the ultrasonic instrument 20 may be a hand-held laparoscopic instrument that may be manually is held and manipulated by an operator. In another embodiment, the instrument may be a part of a surgical robotic arm. Specifically, the ultrasonic instrument may be coupled to a robotic arm and powered by the generator, as described herein. For example, the ultrasonic instrument may be coupled to a distal end of a robotic arm (e.g., arm 4 in FIG. 1), which includes several components that allow the robotic arm to be controlled by an operator. For example, the surgical robotic arm 104 may include a plurality of links and a plurality of actuated joint modules for actuating the plurality of links relative to one another. The joint modules may include various types, such as a pitch joint or a roll joint, which may substantially constrain the movement of the adjacent links around certain axes relative to others. The plurality of the joint modules of the robotic arm 104 can be actuated to position and orient the ultrasonic instrument for robotic surgeries. In one embodiment, the ultrasonic instrument may be coupled to the distal end via a tool drive that is arranged to actuate the end effector 23 of the instrument.

In the case in which the ultrasonic instrument is coupled to a robotic arm, movement and operation of the ultrasonic instrument may be performed via one or more user controls (e.g., UIDs, foot pedals, etc.) that are coupled to the surgical system. For example, a UID may be arranged to open/close the grasper 23 of the ultrasonic instrument, and/or may be arranged to adjust a spatial position (in space) of the grasper based on user input (e.g., the position of the UID.

Figure 3:
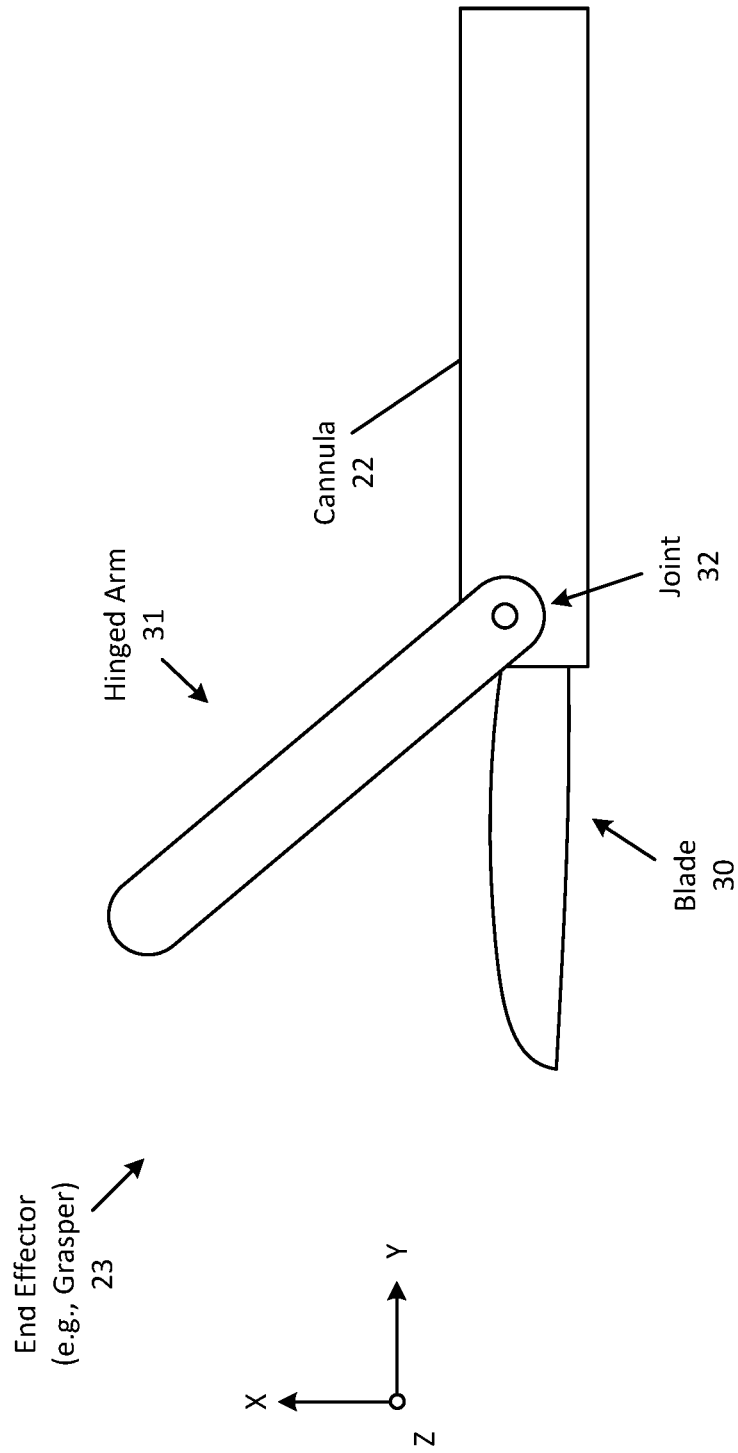
FIG. 3 shows an end effector of the ultrasonic instrument of FIG. 2.

Turning to FIG. 3, this figure shows the end effector 23 of the ultrasonic instrument of FIG. 2. Specifically, this figure shows that the end effector is a grasper (or grasping device) that is received through the cannula 22, and inclues a blade 30 (e.g., as one jaw) and a hinged arm (or jaw) 31 that is rotatably coupled to a joint (or robotic wrist) 32. In particular, the blade is received (and extend) through the cannula and is arranged to couple to the tool drive (e.g., of the hand grip 21), such that the blade vibrates back and further within the cannula. The hinged arm 31 is rotatably coupled (at the joint 32) to the cannula 22, and is arranged to rotate. The grasper is arranged to open and close based on the rotational position of the hinged arm about a rotational axis (e.g., the Z-axis) of the joint with respect to the blade (and/or cannula). For example, the grasper is arranged to open (or is in an opened position) when the hinged arm is rotated away from the blade (e.g., by a threshold distance). While in this position, the end effector may be orientated whereby an object, such as tissue, may be disposed between the blade and the hinged arm (e.g., by moving the end effector about the object). The grasper may be closed (or in a closed position), when the hinged arm rotates towards the blade (e.g., within the threshold distance), whereby the grasper may grab the object between the blade and the hinged arm. As described herein, the hinged arm may be arranged to apply pressure against a grasped object (e.g., squeezing the object between the jaws) in order to grab and/or perform a dissection upon the object.

As described herein, the blade 30 is a jaw of the grasper. In particular, the blade is a jaw that may not rotate (e.g., about the Z-axis) with respect to the end effector. The blade may be arranged to vibrate along a longitudinal axis (e.g., the Y-axis) of the blade to produce heat while the ultrasonic instrument is in a high-power state (or mode). In particular, the blade may be driven (e.g., by the tool drive of the hand grip 21) to move back and forth (e.g., linearly) along the longitudinal axis of the end effector (and through the cannula, as described herein), so as to repeatedly displace the blade 30 at a (e.g., constant) frequency. Specifically, the blade may vibrate (e.g., reciprocate back and forth) over an excursion (or displacement) in which the blade moves a distance (e.g., forward or away from the end effector) from a starting position, and then moves the distance back. In one aspect, the excursion may be a distance the blade moves from a starting position to an extended position. In another aspect, the excursion may be the distance the blade moves forward and backward.

As described herein, the blade may produce frictional heat while vibrating against an object. Specifically, the blade may come into contact with tissue while the grasper is squeezing the tissue between the two jaws, and may vibrate against the tissue. As the blade vibrates, the end effector may cut and/or cauterize the tissue, as described herein. In one aspect, the blade may vibrate differently (e.g., over different excursions) based on a power state of (e.g., how much power is being provided to) the ultrasonic instrument. More about the vibrating blade and the power states of the ultrasonic instrument are described herein.

Turning back to FIG. 2, the generator 25 is configured to control and provide power to ultrasonic instrument to control (e.g., heat) the end effector 23 while the instrument is coupled to the generator and being used by an operator (e.g., during a laparoscopic surgery to manipulate tissue and/or perform one or more surgical tasks upon tissue, such as to cut and seal vessels and/or to cut, grasp, and dissect tissues). In particular, the generator may provide power to the ultrasonic instrument, such that the (e.g., ultrasonic instrument of the) surgical system 1 may operate in one or more power states. For example, the generator may provide power to the instrument such that the ultrasonic instrument is in a "high-power" state (or "heating cycle") in which the instrument draws power (or current) from the generator (e.g., at a particular voltage) to cause the end effector 23 to produce heat. For example, the generator may provide (e.g., a first) current (or input current) to the (e.g., tool drive of the) hand grip of the ultrasonic instrument, which may use this current to drive the blade 30 to vibrate (or oscillate) over a (first) excursion (and at a particular frequency). Frictional heat may be produced by the end effector while the blade of the end effector is vibrating over this excursion up against an object, such as tissue, as described herein. In another aspect, the ultrasonic instrument may be arranged to operate in a "low-power" state (or "cooling cycle") in which the ultrasonic instrument no longer draws the (sufficient or as much) power provided by the generator, while the instrument was in the high-power state, to heat the end effector. Specifically, while in this state, the generator may be configured to provide less power to the ultrasonic instrument than the power provided by the generator while instrument was in the high-power state, such that the end effector does not produce heat (e.g., when in contact with an object). In particular, the generator may provide less current (e.g., a second current) to the ultrasonic instrument than the (first) current provided by the generator while the instrument operates in the high-power state, and as a result, this does not cause the end effector to produce heat (or as much heat as when the ultrasonic instrument is in the high-power state). As a result, the ultrasonic instrument may begin to cool, once it enters the low-power state from the high-power state. Ultimately, if kept in the low-power state, the ultrasonic instrument would drop to (at least) a threshold temperature (e.g., room temperature). In one aspect, the second current may be less than a predefined threshold current. In one aspect, the blade may vibrate at a same frequency in the low-power state as in the high-power state. In another aspect, the blade may vibrate the same within a tolerance frequency range.

As a result, of the lesser current provided to the instrument while in the low-power state, the blade of the end effector may be driven differently by the tool drive 21 than when the instrument is in the high-power state. In particular, the blade may vibrate over a different excursion than over which the blade vibrates while the instrument is in the high-power state. For instance, while in the high-power state, the blade may vibrate over the first (e.g., high) excursion, which may cause the blade to produce heat when pressed against an object, whereas, while in the low-power state, the blade may vibrate over a second (lower) excursion, which may be less than the first excursion (e.g., the blade being displaced less along the longitudinal axis than in the first excursion). In some aspects, the second excursion may be less than a minimum threshold (e.g., at which the blade would produce heat if the blade were to vibrate over the minimum threshold). In one aspect, the end effector may not produce frictional heat, while vibrating over this lower excursion and while up against an object, such as a blood vessel. In one aspect, the resonant frequency is maintained within a tolerance range regardless of which power state the instrument is operating.

In one aspect, the difference in vibration of the end effector may be based on the amount of power that is being drawn by the ultrasonic instrument while in the different states. For instance, the excursion at which the blade is displaced while it oscillates may be based on (e.g., proportional to) the power drawn by the instrument, whereby more power drawn by the instrument may cause the blade to vibrate over the high excursion. Conversely, while the ultrasonic instrument is in the low-power state the instrument may draw less power that causes the blade to vibrate less (than while the instrument is in the low-power state). As a result of oscillating over a lesser displacement, the blade may not produce frictional heat (e.g., while in contact with tissue). In another aspect, the blade may produce some frictional heat while in the low-power state and in contact with an object, but may be less than the heat produced while the instrument is in the high-power state. In this case, this produced frictional heat may not be enough to cut and/or seal tissue. In some aspects, as a result of operating in the low-power state, the end effector of the ultrasonic instrument may enter a cooling cycle, whereby the heat produced by the end effector while the instrument was in the high-power state dissipates (e.g., over a period of time). In another aspect, the blade may not vibrate (e.g., the tool drive 21 may not drive the blade) while in this low-power state.

In one aspect, the system may enter (or operate in) at least one of the power states based on user input (e.g., received by the generator 25). In particular, the generator may provide power to the ultrasonic instrument based on receiving user input into one or more input devices (e.g., input into a foot petal, an UID that is controlled by an operator and communicatively coupled with the system 1, and/or input at the hand grip 21 of the ultrasonic instrument). The provided power based on the user input may put the ultrasonic instrument in the high-power state in which the ultrasonic instrument draws power from the generator to heat the (e.g., blade 30 of the) end effector 23. For example, when the generator receives (a first) user input (e.g., by the operator pulling on or pressing a trigger on the hand grip 21), the generator may provide current to the (e.g., tool drive 21 of the) ultrasonic instrument, which uses the current to drive the end effector, as described herein. Thus, in the case where the trigger controls the hinged arm of the end effector, the generator is configured to provide the current when the hinged arm is moved (e.g., towards the blade 30 by at least a threshold distance). In another aspect, the system may enter the low-power state based on another (e.g., second) user input (e.g., receiving input from a different input device coupled to the generator, such as a foot pedal).

In some aspects, the ultrasonic instrument may be arranged to switch between the high-power state and the low-power state. As described herein, the instrument may operate in the high-power state while the generator is receiving user input (e.g., the user pulling on or pressing a trigger on the hand grip). The instrument may operate in the low-power state in response to the generator not receiving user input. For instance, the ultrasonic instrument may switch from the high-power state into the low-power state in response to the user releasing the trigger on the hand grip, the generator may transition between the two states). In one aspect, the instrument may operate in the low-power state while the operator is not actively using the instrument to perform ultrasonic instrument operations, as described herein. Specifically, the system may enter the low-power state, while user input is not received into one or more input devices that are used by the operator to enter the high-power state. Once, however, the operator wishes to actively use the ultrasonic instrument, the ultrasonic instrument may switch back into the high-power state (e.g., in response to user input). In another aspect, the instrument may operate in the low-power state in response to receiving user input (e.g., the user pressing a button on a UID). In another aspect, the instrument may operate in this state for a period of time. As described herein, the surgical system is configured to determine a temperature of the end effector while in the low-power state (e.g., after switching from the high-power state) in order to notify an operator of the temperature, which may be high due to the instrumenting having operated in the high-power state. Once the end effector cools to a particular temperature (e.g., equal to or below a predefined temperature), the generator may deactivate the instrument by ceasing to provide the lower current, since at this temperature the end effector may not cause thermal injuries if it were to come into contact with tissue.

In one aspect, the generator may provide different levels of current to heat up the blade, which may be based on user input. For instance, the generator may receive a first user input (e.g., from one petal coupled to the generator) and, in response, provide the ultrasonic instrument with a maximum (allowable) amount of current. The ultrasonic instrument may then drive the end effector over a maximum (e.g., predefined) excursion, which may result in the end effector producing heat at a (first) high temperature. When the generator receives a second user input (e.g., from another petal coupled to the generator), however, the generator may provide a lesser amount of current to the ultrasonic instrument. As a result, the ultrasonic instrument may draw less power to cause the end effector to vibrate over a (second) lower excursion, which may be lower than the first excursion over which the blade vibrates in response to the first user input. This lower excursion, however, may cause the end effector to heat at a lower temperature than the first temperature of the end effector when the ultrasonic instrument draws more current (in response to the generator receiving the first user input). By heating the end effector to different temperatures, different types of tissues may be cut and/or cauterized. For example, fattier tissues may require the end effector to be hotter (having the first temperature), whereas thinner (and less fatty) tissues may require less heat (having the second temperature), in order to cut and/or cauterize the tissues. In another aspect, the generator may be configured to provide one current while in the high-power state (e.g., to drive the end effector over the first high excursion).

As described herein, the ultrasonic instrument may be activated (e.g., operate in the high-power state) based on whether the end effector is in a closed position so as to grasp an object (e.g., a piece of tissue). For example, the ultrasonic instrument may be (e.g., user) activated, such that the ultrasonic instrument may operate in the high-power state so as to draw enough current to cause the end effector to produce heat. In particular, the generator may activate the ultrasonic instrument upon receiving user input to close the end effector (e.g., to cause the hinged arm 31 to move within a distance of the blade 30). Once user input is received to move the hinged arm, the generator may be configured to provide (e.g., enough) power to activate the instrument, as described herein. In some aspects, the generator may activate the instrument based upon a determination that the hinged arm and/or the blade are in contact with an object. For instance, the ultrasonic instrument may include one or more sensors (e.g., force sensors), that detect a presence of an object and/or detect that an object is in contact with both arms. Upon making this determination, the generator may provide the first current to oscillate the blade in order to cause the blade to produce heat.

In one aspect, the (e.g., generator of the) surgical system may be configured to determine one or more characteristics of the ultrasonic instrument, while the instrument is in one or more of the power state. For example, the generator may be configured to keep track (or monitor) characteristics, such as an input voltage, an input current, a resonance state, and/or a resonance frequency of the ultrasonic instrument. In one aspect, the generator may be configured to monitor at least some of these characteristics of the instrument, while the instrument operates in the high-power state. Unlike conventional systems, however, that are unable to determine characteristics while an ultrasonic instrument is in the cooling cycle because the instrument is deactivated (e.g., no power being provided by the generator), the surgical system of the present disclosure is able to determine the characteristics while the instrument is in the low-power state (or cooling cycle) due to the instrument drawing at least some power. For example, the generator may determine the resonance frequency of the (e.g., blade 30 of the) end effector, while in the low-power state.

In one aspect, at least one of the characteristics of the ultrasonic instrument may be determined from other characteristics. For instance, one characteristic may be a change in resonance frequency of the (blade of the) end effector. The generator may determine the change based on one or more (e.g., previously) monitored resonance frequencies. For example, a change in resonance frequency may be determined based on a comparison between (at least) one previously determined frequency and a most recently determined resonance frequency. In another aspect, the change in resonance frequency may be an average change over a period of time (or over a number of samples taken by the generator).

In one aspect, the surgical system may include additional components. For example, the system may include a cable that connects the generator to the ultrasonic instrument (e.g., the ultrasonic transducer, which is configured to convert an electric current drive signal to mechanical vibrations). In one aspect, the ultrasonic transducer may be connected to a waveguide, which is connected to the blade 30 of the end effector 23.

Also shown, the generator 25 also includes a display 24, which is arranged to disclose information regarding the operation of the ultrasonic instrument. For instance, the display may present temperature information, which state the ultrasonic instrument is currently in, and one or more of the characteristics described herein.

Figure 4:
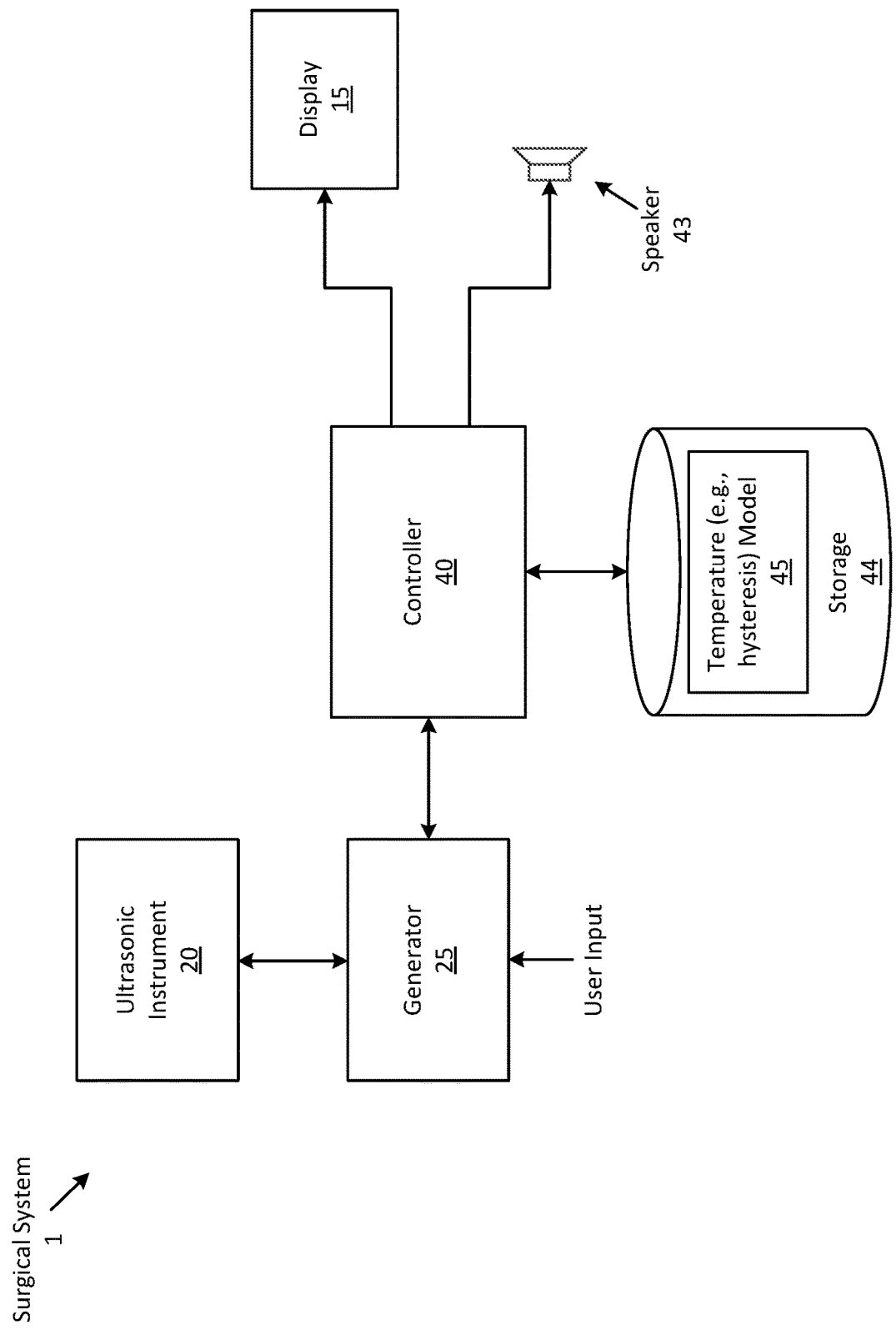
FIG. 4 is a block diagram of the surgical system according to one aspect.

FIG. 4 is a block diagram of the surgical system 1 according to one aspect. The system includes the ultrasonic instrument 20, the generator 25, a controller 40, the display 15, and a speaker 43 (that may be a stand-alone speaker or a part of an electronic device of the system, such as the user console 2). In one aspect, the system may include more or less elements, such as having more than one display and/or not having the speaker.

In one aspect, controller 40 may be a special-purpose processor such as an application-specific integrated circuit (ASIC), a general purpose microprocessor, a field-programmable gate array (FPGA), a digital signal controller, or a set of hardware logic structures (e.g., filters, arithmetic logic units, and dedicated state machines). In one aspect, the controller may be a part an electronic device, such as the console computer system 16, the control tower 3, and/or the user console 2. Although illustrated as being a single component, in one aspect the controller may comprise one or more electronic components (e.g., processors, memory, etc.) that are communicatively coupled on a single electronic device (such as the console computer 16), or across multiple devices (e.g., communicating over a wireless computer network). In some aspects, the controller may be a part of a separate device, such as a part of a remote server that is in communication with one or more electronic devices. In another aspect, the controller may be a part (e.g., at least partially integrated within) the generator 25. In which case, at least some of the other elements (e.g., the speaker and display) may also be a part of (integrated within) the generator. As a result, at least some of the operations performed by the controller described herein may be performed by the generator.

As described herein, the controller is configured to perform temperature estimation operations for the surgical system 1 to determine a (e.g., real-time) temperature of the (e.g., end effector of the) ultrasonic instrument, while the instrument is in use by an operator of the system. Specifically, the controller may determine the temperature based on one or more characteristics (e.g., a resonance frequency) of the ultrasonic instrument that are determined while the instrument is in the high-power state (e.g., being actively used by the operator to perform a surgical task, such as cut and/or seal tissue) and/or while the instrument is in the low-power state (e.g., not actively being used by the operator to perform a surgical task). In particular, the controller may be configured to apply the one or more characteristics to a temperature (e.g., hysteresis) model 45 that is stored in memory (storage) 44. More about the operations performed by the controller to estimate temperature is described herein. At least some of the operations performed by the controller may be implemented in software (e.g., as instructions) stored in memory of the surgical system (and/or stored in memory of the controller) and executed by the controller and/or may be implemented by hardware logic structures. In one aspect, at least some of the operations performed by the controller may be performed in real-time (e.g., while the instrument operates in one of the one or more power states).

As shown, the generator may receive user input (e.g., via one or more electronic devices coupled to the generator) for causing the generator to perform one or more operations. For instance, the user input may be received via the ultrasonic instrument (e.g., when the user pulls on a trigger of the hand grip) in order to cause the generator to provide current that causes the ultrasonic instrument to switch from the low-power state to the high-power state, as described herein.

The storage (or memory) 44 stores a temperature model 45 that is for estimating (or determining) a temperature of the end effector 23 of the ultrasonic instrument from one or more characteristics. In one aspect, the temperature model may be a model that is predefined in a controlled environment (e.g., a laboratory). More about defining the model is described herein. In some aspects, the model may be a hysteresis model that includes (or defines) a hysteretic relationship between one or more characteristics of the ultrasonic instrument and one or more (corresponding) temperature values of the (e.g., end effector 23 of the) ultrasonic instrument 20. For instance, the model may define (e.g., non-linear behavior of) temperature of the end effector (e.g., the blade of the end effector) of the instrument with respect to characteristics, such as one or more changes in resonance frequency of the (e.g., blade of the) end effector. For example, when a blade of an ultrasonic instrument heats up during an activation (heating) cycle (e.g., while the instrument is in the high-power state), material properties of the blade (e.g., stiffness) change, which are reflected by changes in the blade's resonance frequency. These changes in resonance frequency are reversed back as the blade enters the cooling cycle (e.g., while in the low-power state) to cool down (e.g., to room temperature), though the resonance frequency does not follow the same exact rate and path as it did during the heating cycle. As a result, there is a hysteresis relationship between the resonance frequency change of the blade and the blade temperature. More about this hysteresis relationship is described herein.

In one aspect, the hysteresis temperature model 45 may be any hysteresis model that defines a relationship between resonance frequency and temperature. For example, the model may be a discretized Preisach model of hysteresis that models an output function as a weighted sum of individual relay functions, called hysterons. In one aspect, each hysteron, $\gamma$, has a distinct turn on and turn off threshold (e.g., $\alpha$ and $\beta$, respectively), and contributes a "+1" or "-1" value (when turned on and off, respectively) to a summation that depends on the value of the input. In one aspect, the model may have one or more hysterons, which may be defined as $\gamma_{\alpha 1 \beta 1} \ldots \beta_{\alpha n \beta n}$. In one aspect, each hysteron may be associated with (e.g., a different) weight factor, $\mu$, that defines an individual contribution of each hysteron to the summed weight. Thus, each of the hysterons, $\gamma_{\alpha 1 \beta 1} \ldots \gamma_{\alpha n \beta n}$ may be associated with a respective weight factor, $\mu_{\alpha 1 \beta 1} \ldots \mu_{\alpha n \beta n}$. In some aspects, at least some of the hysterons may include different (or a same) turn on/off thresholds and/or weighted factors. With respect to the temperature model, the turn on/off thresholds may correspond to changes, such as increasing (or positive) or decreasing (or negative) changes in resonance frequency of the end effector. In which case, changes in resonance frequency may be input to the model, which outputs a temperature of the end effector that may be a summation of one or more (e.g., weighted factors of the) hysterons of the hysteresis model. More about using the model to determine the temperature of the end effector is described herein.

Figure 5:
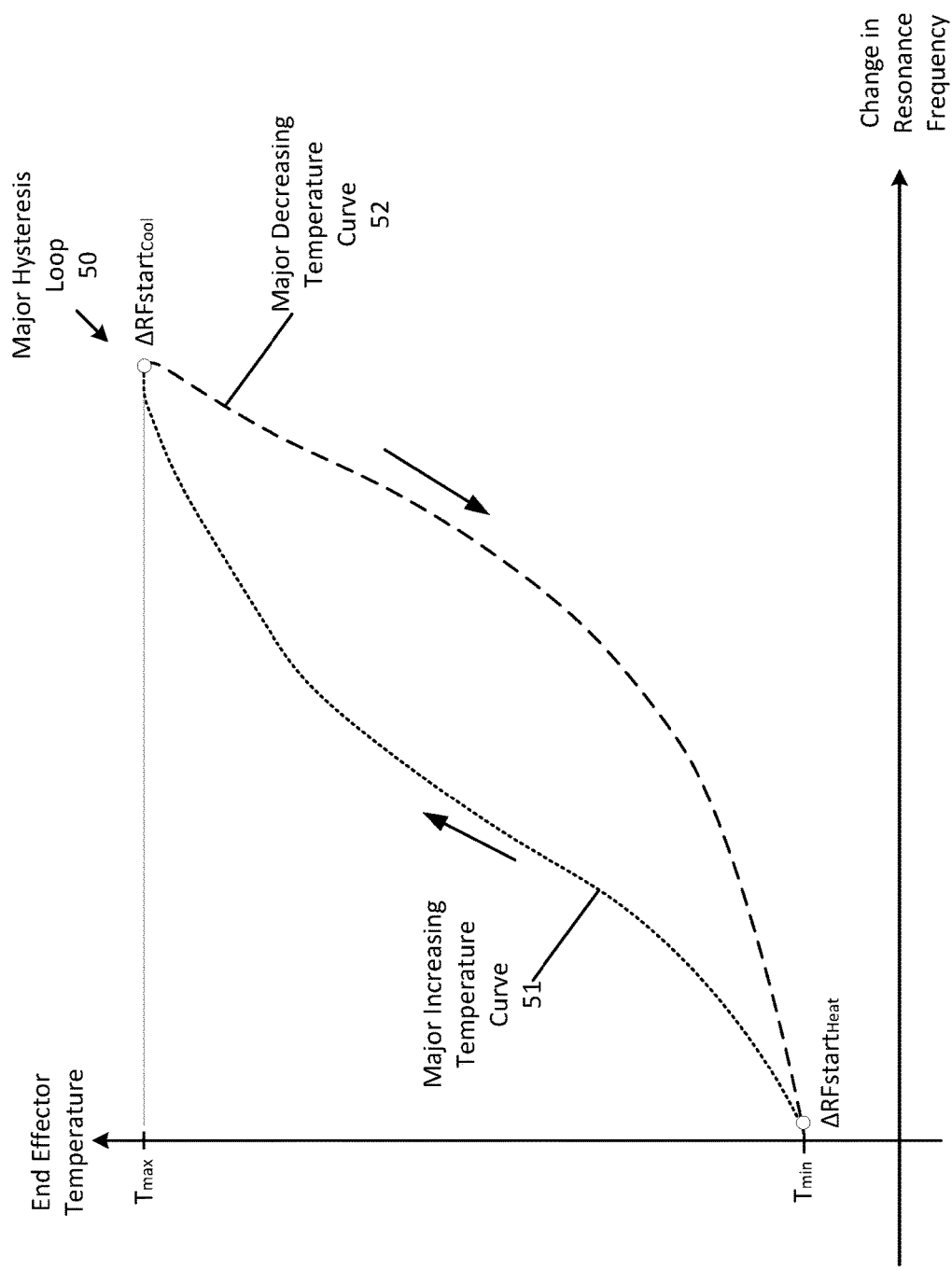
FIG. 5 shows a graphical representation of a hysteresis loop of a hysteresis model according to one aspect.

In some aspects, the hysteresis model 45 may include (or define) a hysteresis loop with temperature values of the ultrasonic instrument's end effector with respect to changes in the end effector's resonance frequency (e.g., while the instrument is in use). This is due to the hysteretic relationship between the temperature and changes in resonance frequency, as described herein. Turning now to FIG. 5, this figure shows a graphical representation of a major hysteresis loop 50 of the model according to one aspect. The loop includes a major increasing (or first) temperature curve 51 and a major decreasing (or second) temperature curve 52, both having (at least some) different temperature values with respect to (e.g., the same or similar) changes in resonance frequency of the end effector.

In one aspect, the hysteresis loop 50 represents the temperature behavior of the end effector while the ultrasonic instrument is in use. Specifically, the first temperature curve 51 represents several temperature values of the end effector during a heating cycle from which the end effector starts at a minimum temperature, $T_{min}$, such as room temperature or a predefined temperature, to a maximum temperature, $T_{max}$, of the end effector. In some aspects, $T_{max}$ may be a predefined temperature, such as defined by a specification of the manufacturer of the end effector. As shown, the first curve 51 begins at a starting change in resonance frequency during a heating cycle, $\Delta RFstart_{Heat}$, where the temperature of the end effector is at (or near) a minimum temperature, $T_{min}$. In one aspect, $\Delta RFstart_{Heat}$ may represent the change in resonance frequency of the end effector when the ultrasonic instrument enters a heating cycle (e.g., is activated) to perform a surgical task upon a piece of tissue (e.g., once the ultrasonic instrument is in the high-power state). In another aspect, $\Delta RFstart_{Heat}$ may be a change in resonance frequency after a period of time from which the instrument was activated. As the change in resonance frequency of the end effector increases, curve 51, due to an increase of heat produced by the end effector, the temperature values increase. The curve 51 represents the heating behavior of the end effector from a minimum temperature to a maximum temperature, while the ultrasonic instrument is in the high-power state, causing the end effector to produce heat. Thus, the temperature values of the curve 51 increase with respect to increasing changes in resonance frequency.

The second temperature curve 52 represents several temperature values of the end effector during a cooling cycle from when the end effector is at $T_{max}$, to when the end effector is cooled down to the minimum temperature, $T_{min}$. As shown, the second curve 52 begins at a starting change in resonance frequency during (or at the beginning of) the cooling cycle, $\Delta RFstart_{Cool}$, where the temperature of the end effector is at or near $T_{max}$. In one aspect, $\Delta RFstart_{Cool}$, may represent the change in resonance frequency of the end effector once (or after a period of time) the ultrasonic instrument is no longer active, and is in the low-power state. For instance, this change may occur after user-input is received to switch the end effector from the high-power state to the low-power state, resulting in the end effector beginning a cooling cycle. As the change in resonance frequency of the end effector decreases, the curve 52 (or temperature values of the curve) decrease. The second curve 52 ends at $T_{min}$. Thus, the temperature values of the curve 52 decrease with respect to decreasing changes in resonance frequency. In one aspect, each change in resonance frequency (along the X-axis) is associated with two temperatures values (e.g., along the Y-axis): one temperature value along the major decreasing temperature curve 52 and another temperature value along the major increasing temperature curve 51, which is greater than the temperature value along curve 52.

In one aspect, this hysteretic relationship between the resonance frequency change and the end effector temperature during the heating and cooling cycles, may be due to a delay caused by the heat capacitance build up and the thermal gradient that occurs across the (e.g., blade) of the end effector. Specifically, while the blade heats up, the temperature of the overall structure rapidly increases inducing a shift in the resonance frequency, however, while cooling down, although the blade temperature falls down, the residual heat remaining in the rest of the structure causes a slower progress in restoring the resonance frequency. Therefore, both curves of follow different temperature patterns to form the hysteresis loop.

In one aspect, the change in resonance frequency may be a continuous change in the end effector's blade's resonance frequency during use. For example, as the blade heats, its resonance frequency may increase. Specifically, a current resonance frequency measurement of the blade may increase (e.g., slightly) with respect to a previously measured resonance frequency. In one aspect, the major hysteresis loop 50 may reflect this increase, such as in curve 51. Conversely, if a subsequent resonance frequency measurement is less than a previous measurement, the change in resonance frequency decreases (or is reduced), which is reflected in the direction of curve 52 moving from $T_{max}$ to $T_{min}$.

As described herein, the hysteresis loop 50 shows the temperature behavior of the end effector with respect to changes in resonance frequency as the end effector is heated from a minimum temperature to its maximum temperature, and then back again to its minimum temperature. This behavior may occur during use of the ultrasonic instrument. For example, an operator may activate the ultrasonic instrument by having the instrument (begin to) operate in the high-power state to heat the end effector to its maximum temperature to perform a task. Once the task is completed, the instrument may be switched to the low-power state, allowing the end effector to cool (e.g., by entering a cooling cycle) to its minimum temperature. In some cases, however, the operator may re-activate the ultrasonic instrument while it cools (e.g., while a current temperature of the end effector is along the major decreasing temperature curve 52 but before reaching $T_{min}$). Conversely, an operator may choose to switch the instrument to the low-power mode before the instrument reaches $T_{max}$. As a result, the end effector may follow one or more different temperature curves that are contained within the hysteresis loop based on when the ultrasonic instrument switches between heating and cooling cycles.

Figure 6:
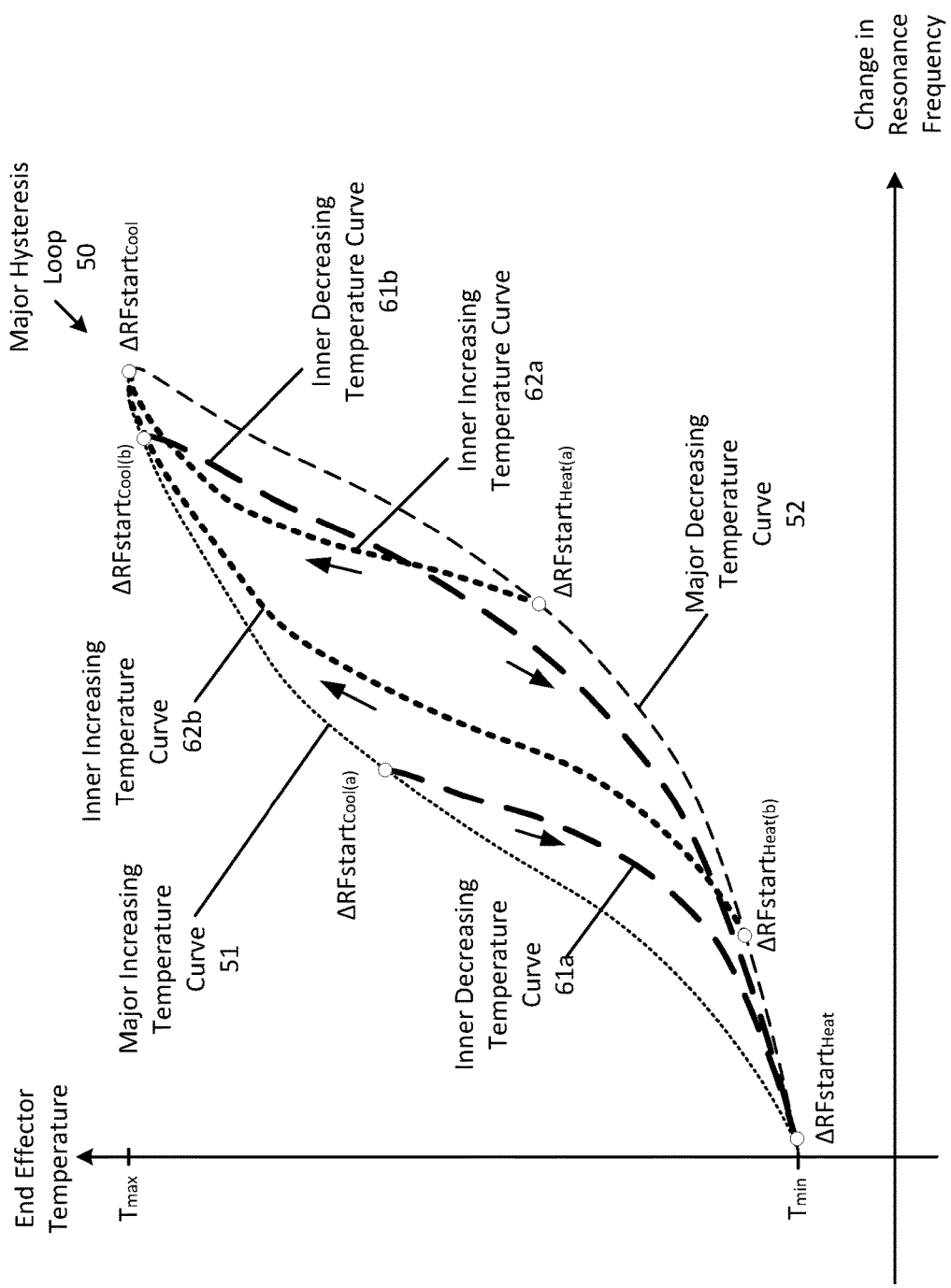
FIG. 6 shows a graphical representation of the hysteresis loop with several inner temperature curves contained therein according to one aspect.

Turning to FIG. 6, this figure shows a graphical representation of the hysteresis loop with several inner temperature curves contained therein according to one aspect. Specifically, this figure is showing several inner temperature curves of the temperature model 45 that represent temperature behavior of the end effector as the ultrasonic instrument switches between heating and cooling cycles (e.g., switches between the high-power state and the low-power states). For example, there are two inner decreasing temperature curves 61a and 61b, and two inner increasing temperature curves 62a and 62b, where each of the curves represent the temperature behavior of the ultrasonic instrument (e.g., having one or more temperature values) with respect to changes in resonance frequency as the end effector of the instrument cools and heats, respectively.

As shown, each of the inner decreasing temperature curves 61a and 61b start at a different change in resonance frequency, and decrease with respect to changes in resonance frequency (e.g., to or about $T_{min}$). Inner curve 61a starts at $\Delta RFstart_{Cool(a)}$ and inner curve 61b starts at $\Delta RFstart_{Cool(b)}$, which is greater than $\Delta RFstart_{Cool(a)}$ In one aspect, each of these inner decreasing temperature curves represent temperature behavior of the end effector, when the ultrasonic instrument switches from a heating cycle (e.g., in which the temperature of the end effector tracks curve 51) to a cooling cycle. Each of the inner increasing temperature curves 62a and 62b start at a different change in resonance frequency, and increase with respect to changes in resonance frequency (e.g., to or about $T_{max}$). Inner curve 62a starts at $\Delta RFstart_{Heat(a)}$ and inner curve 62b starts at $\Delta RFstart_{Heat(b)}$; which is less than $\Delta RFstart_{Heat(a)}$. Thus, each of the inner increasing temperature curves represent temperature behavior of the end effector, when the ultrasonic instrument switches from a cooling cycle (e.g., in which the temperature of the end effector tracks curve 52) to a heating cycle.

In one aspect, the temperature model 45 may include more or less inner curves, each of which have different (or same) starting changes in resonance frequencies. As shown, the starting resonance frequencies of the inner curves are along the major hysteresis loop 50. In another aspect, at least some starting resonance frequencies for at least some inner (e.g., decreasing and/or increasing) curves may be inside the hysteresis loop, due to the ultrasonic instrument switching cycles while tracking an inner curve. In some aspects, the model may include (at least some) of the curves of the hysteresis loop, such as in one or more tables that associate one or more temperatures with one or more changes in resonance frequency, according to the (e.g., major and/or inner) curves. In another aspect, the model may be configured to output one or more temperatures values based on one or more changes in resonance frequency. In which case, temperature values that are output by the model may be based on (or track) one or more of the (major and/or inner) curves, described herein. More about determining the temperature of the end effector using the model is described herein.

Figure 7:
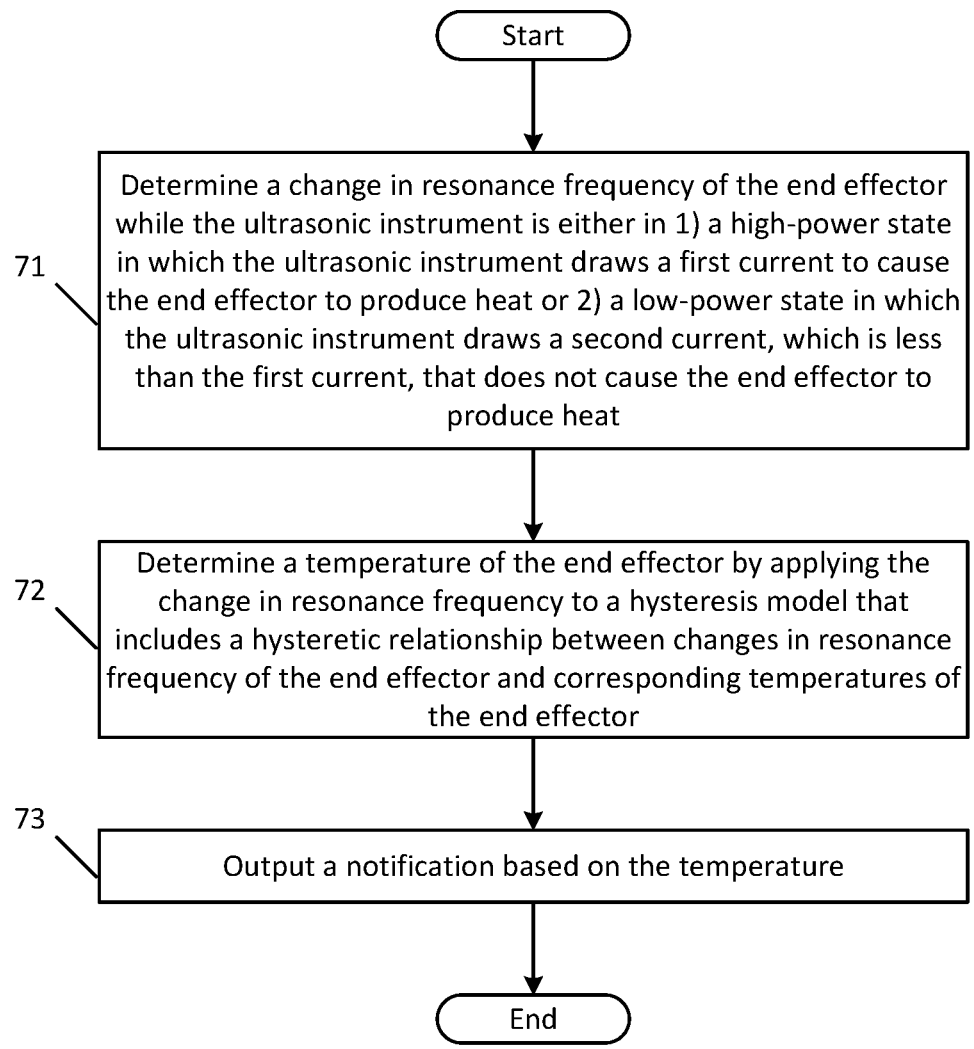
FIG. 7 is a flowchart of a process for estimating a temperature of an end effector of the ultrasonic instrument while the instrument is being used by an operator of the surgical system.

Turning now to FIG. 7, this figure is a flowchart of a process 70 for estimating a temperature of an end effector of the ultrasonic instrument while the instrument is being used by an operator of the surgical system 1. In particular, at least some of these operations may be performed once and/or while the ultrasonic instrument is in either of the one or more power states described herein. For example, the surgical system may perform one or more of the operations of this process while the ultrasonic instrument receives power from (e.g., the generator 25 of) the surgical system 1. In one aspect, the process may be performed one or more times, while the instrument receives power in order to continuously estimate the temperature of the instrument's end effector (e.g., in real-time). Thus, the temperature of the instrument's blade may be estimated during (and/or between) heating and/or cooling cycles of the instrument that are based on the power state of the instrument. In one aspect, the process may be performed by one or more components of the surgical system 1, such as being performed by the controller 40. As another example, at least some operations may be performed (e.g., by one or more processors of) the generator 25. Thus, this figure will be described with reference to FIGS. 4-6.

The process 70 begins by the controller 40 determining a change in resonance frequency of the (e.g., blade of the) end effector 23 while the ultrasonic instrument is either in 1) a high-power state in which the ultrasonic instrument draws a first current to cause the end effector to produce heat or 2) a low-power state in which the ultrasonic instrument draws a second current, which is less than the first current, that does not cause the end effector to produce the heat (at block 71). In particular, the controller 40 may receive one or more resonance frequency measurements of the ultrasonic instrument (e.g., from the generator 25). In which case, the controller may determine the change based on a comparison between a (e.g., currently) determined resonance frequency of the instrument and a previously determined resonance frequency (e.g., the resonance frequency that was measured immediately before the currently determined frequency). For instance, the change may be a difference between the current and previous resonance frequency. In which case, the change in resonance frequency may increase when the difference is positive, and may conversely decrease when the difference is negative. In another aspect, the change may be based on a comparison of two or more determined resonance frequencies.

In another aspect, the change in resonance frequency may be based on a starting resonance frequency determined (e.g., from the generator 25). As described herein, the surgical system may be configured to use one or more (e.g., different) ultrasonic instruments (e.g., having one or more different types of components, such as different blades). Each ultrasonic instrument may have a slightly different starting resonance frequency due to minor differences (e.g., which may be due to differences in manufacturing). As a result, each ultrasonic instrument may have a different starting resonance frequency, which may be determined by the surgical system when the instrument is first turned on. For instance, the system may determine the starting resonance frequency when the instrument is first powered up and operating in the low-power state and while the instrument (e.g., blade) is cold and unused. The controller 40 may be configured to determine the changes in resonance frequency from this starting resonance frequency. In some aspects, the staring resonance frequency may be determined each time the (e.g., ultrasonic instrument of the) surgical system is activated for a surgical operation.

The controller 40 determines a temperature of the end effector by applying the change in resonance frequency to a hysteresis model (e.g., model 45 of FIG. 4) that includes a hysteretic relationship between changes in resonance frequency of the end effector and corresponding temperatures of the end effector (at block 72). For example, the controller may retrieve the model 45 from storage 44 of the surgical system 1, and may apply the change in resonance frequency and may receive the temperature of the end effector as output. In some aspects, the controller may determine the temperature (e.g., in real-time) using a hysteresis model, such as the discretized Preisach model, as described herein. For example, the application of the change in resonance frequency may adjust hysterons within the model, thereby determining a (e.g., current) temperature of the end effector. More about the use of the Preisach model is described herein.

As described herein, the model may include a hysteresis loop (e.g., major loop 50), and one or more inner curves. In one aspect, the temperature may be determined based on these curves. For example, the controller may identify the temperature that is associated with the change in resonance frequency, using one or more of the curves of the model. For instance, as the change in resonance frequency increases (which may be due to the ultrasonic instrument being in the high-power state), the controller may use the major increasing temperature curve 51 to identify the temperature (on the curve) that corresponds to the change in resonance frequency. Conversely, as the change in resonance frequency decreases (e.g., while the ultrasonic instrument is in the low-power state), the controller may use the major decreasing temperature curve 52 to identify the temperature (on the curve) that corresponds to the change in resonance frequency. In another aspect, the model may include one or more tables (e.g., the curves may be stored in one or more tables), with which the controller determines the temperature. For example, the temperature may be determined by performing a table lookup into a table that associates changes in resonance frequency with one or more temperature values of the end effector.

The controller outputs a notification based on the temperature (at block 73). For example, the controller may display a (e.g., pop-up) notification that includes the temperature of the end effector on the display 15 of the surgical system 1. In which case, the displayed notification may be a graphical user interface (GUI) item that is overlaid on video and/or images that are being displayed on the display, such an endoscopic video, which may be provided by an endoscopic camera that has a field of view of a surgical site (e.g., within an abdomen of a patient). In another aspect, the notification may indicate a status (e.g., "Hot" or "Cool") of the end effector. In another aspect, the system may output an audible notification through the speaker 43. For instance, the audible notification may be one or more sounds (e.g., a beep), which indicates that the end effector has a temperature that is above a threshold. Once the end effector has cooled below the threshold (or has reached another threshold, such as $T_{min}$), the system may cease to output the sounds. In another aspect, the audible notification may be spoken word (e.g., "Caution! The Blade is Hot!"). In another aspect, any type of notification may be used.

In one aspect, the controller may perform one or more of these operations in real-time (e.g., while the ultrasonic instrument is in use by the operator), such that the surgical system 1 may (e.g., continuously) estimate and provide (e.g., a notification of) the temperature to the operator. In which case, the controller may continue to display the temperature of the end effector, while the ultrasonic instrument is in the high-power and/or low-power state. In some aspects, the system may cease providing the notification upon determining that the temperature of the end effector reaching a threshold, as described herein. For instance, the controller may determine whether the temperature is less than a temperature threshold. In response to determining that the temperature is above the threshold, the controller may (e.g., continue to) output the notification. If, however, the temperature is less than the threshold, the controller may cease outputting the notification, which may provide the operator the indication that the end effector is no longer hot. In another aspect, the controller may output a notification that the end effector is no longer hot (e.g., by displaying a pop-up notification on the display, such as "The Blade is Cool".

In some aspects, the controller may be configured to determine a time at which the temperature of the end effector will be below a temperature threshold. For instance, as described herein, the controller determines the temperature of the end effector based on changes in the resonance frequency. In which case, the controller may use the model to estimate when the blade will be below the temperature threshold based on a rate of change of the temperature with respect to time. For example, the model 45 may include periods of time (or a rate of change) for which a curve of the hysteresis loop takes to reach $T_{max}$ or $T_{min}$, from its starting change in resonance frequency. Thus, the controller may determine the time based on the rate of change of the model. Once determined, the controller may be configured to include the time with the notification in order to provide the operator an indication as to when the end effector will be cool or hot (e.g., time it takes to reach $T_{max}$) or another threshold temperature.

Some aspects may perform one or more variations of the process 70 described herein. For example, the specific operations of the process may not be performed in the exact order shown and described. The specific operations may not be performed in one continuous series of operations and different specific operations may be performed in different aspects.

As described herein, the surgical system 1 is configured to determine the temperature of the end effector based on one or more changes in resonance frequency. Thus, the system determines the temperature using one or more signal processing operations (e.g., by applying changes in resonance frequency to the temperature model, as described herein), without the use of temperature data from a temperature sensor. In some aspects, the system may not include a temperature sensor (e.g., an infrared temperature sensor, such as a thermocouple, etc.).

Figure 8:
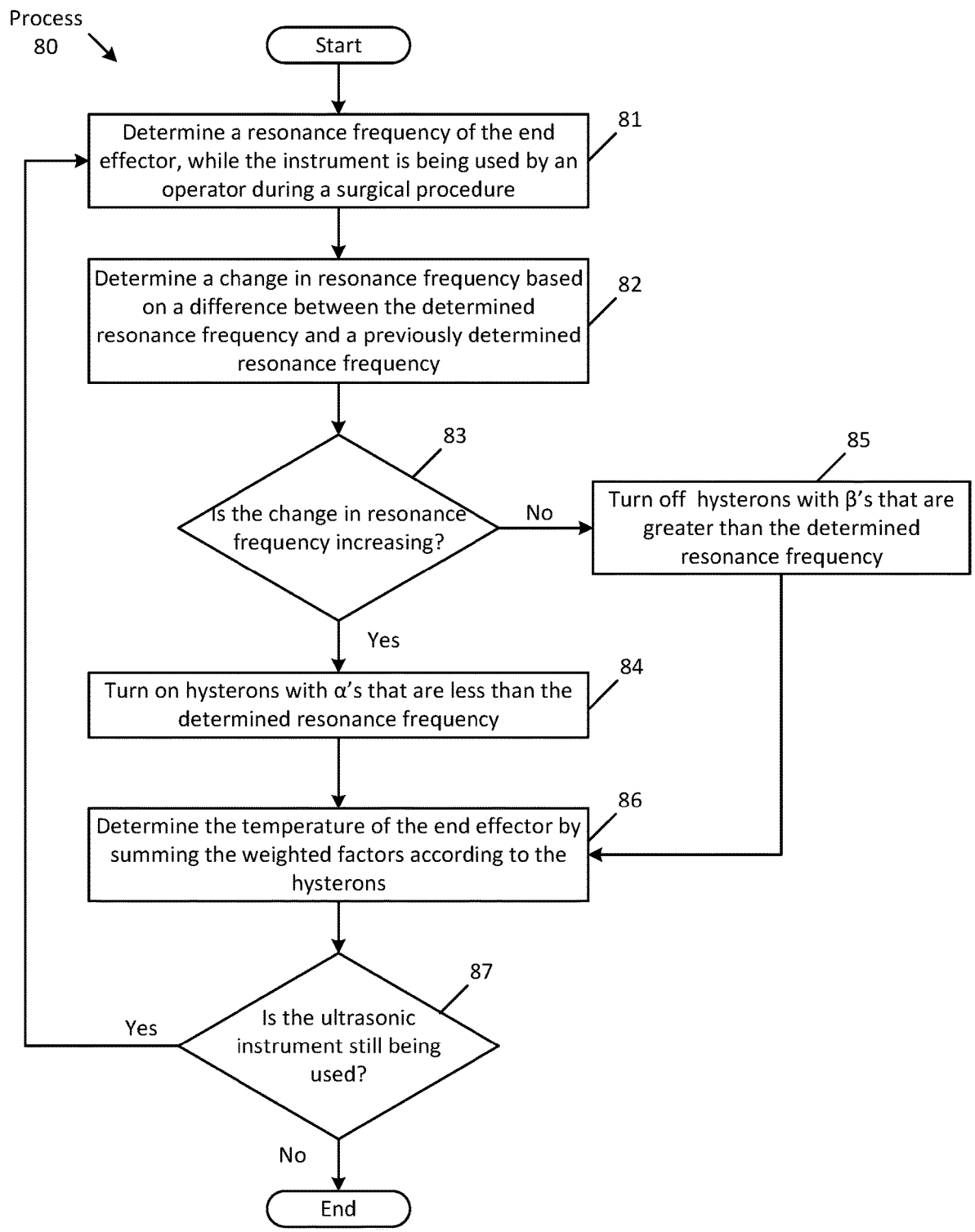
FIG. 8 is a flowchart of a process for using a hysteresis model to determine the temperature of the ultrasonic instrument.

FIG. 8 is a flowchart of a process 80 for using a hysteresis model to determine the temperature of the ultrasonic instrument. Specifically, at least some of the operations described in this process may be performed in block 72 of process 70 of FIG. 7 for determining the temperature of the end effector using the hysteresis model 45 described in FIG. 4. In one aspect, the operations may be performed by the surgical system 1 (e.g., the generator 25 and/or the controller 40). The process 80 begins by the controller determining a resonance frequency of the end effector, while the ultrasonic instrument is being used by an operator during a surgical procedure (at block 81). In one aspect, the resonance frequency may be received by the generator 25, while the ultrasonic instrument is in any of the power states (e.g., high-power or low-power) described herein. The controller determines a change in resonance frequency based on a difference between the determined resonance frequency and a previously determined resonance frequency (at block 82). In one aspect, the change may be a positive value, indicating that the change is increasing, conversely, if the change is a negative value, this may indicate that the change is decreasing. This may be illustrated in FIG. 5, where if the change is a positive value, the change in resonance frequency may move in a positive x-direction (from a previously determined change in resonance frequency) by the amount of the change.

The controller 40 determines if the change in resonance frequency is increasing (at decision block 83). In one aspect, this may be determined based on whether the change is a positive value. If so, the controller turns on hysterons with $\alpha$'s that are less than the determined resonance frequency (at block 84). In one aspect, the hysterons that are turned on contribute a positive weighting factor value to the output of the end effector temperature (e.g., $+\mu$). The controller determines the temperature of the end effector by summing the weighted factors according to the hysterons (at block 86). Specifically, the temperature is determined by summing all of the weighting factors coming from all of the hysterons.

If the change is not increasing, but rather is decreasing, the controller turns off hysterons with $\beta$'s that are greater than the determined resonance frequency (at block 85). Specifically, the change may be decreasing when the change (difference between the currently determined resonance frequency and a previously determined frequency) is a negative value. In this case, the hysterons that are turned off contribute a negative weighting factor value to the output (e.g., $-\mu$). In one aspect, the determination of which hysterons to turn on (and/or turn off) may be based on the change in resonance frequency. For example, when the change is decreasing, the controller may turn off hysterons with $\beta$'s that are greater than the determined change in resonance frequency. The controller then determines the temperature by summing the factors for all hysterons at block 86, as described herein.

In one aspect, the determined temperature may increase or decrease (from a current temperature of the end effector that was previously determined) based on whether the change is increasing or decreasing. For example, when the change in resonance frequency is a positive value the determined temperature may be a first temperature, whereas when the change in resonance frequency is a negative value the determined temperature may be a second temperature that is less than the first temperature. In particular, the first temperature may be greater than a previously determined temperature, whereas the second temperature may be less than a previously determined temperature.

The controller determines if the ultrasonic instrument is still being used (at block 87). For example, the controller may determine whether the ultrasonic instrument is in either of the power states or whether the ultrasonic instrument is deactivated (e.g., the generator turned off). If the ultrasonic instrument is in a power state, the controller may return to block 81 to determine the temperature of the end effector. Thus, the controller may continuously determine the temperature while the ultrasonic instrument is in use.

Some aspects perform one or more variations of the process 80 described herein. For example, the specific operations of the process may not be performed in the exact order shown and described. The specific operations may not be performed in one continuous series of operations and different specific operations may be performed in different aspects. As described herein, the process may turn on/off hysterons based on whether the change in resonance frequency is increasing or decreasing, respectively. In one aspect, if the change is equal to (or approximately) zero, meaning that the resonance frequency has not changed, the controller may determine the temperature not have changed from a previous determination.

Figure 9:
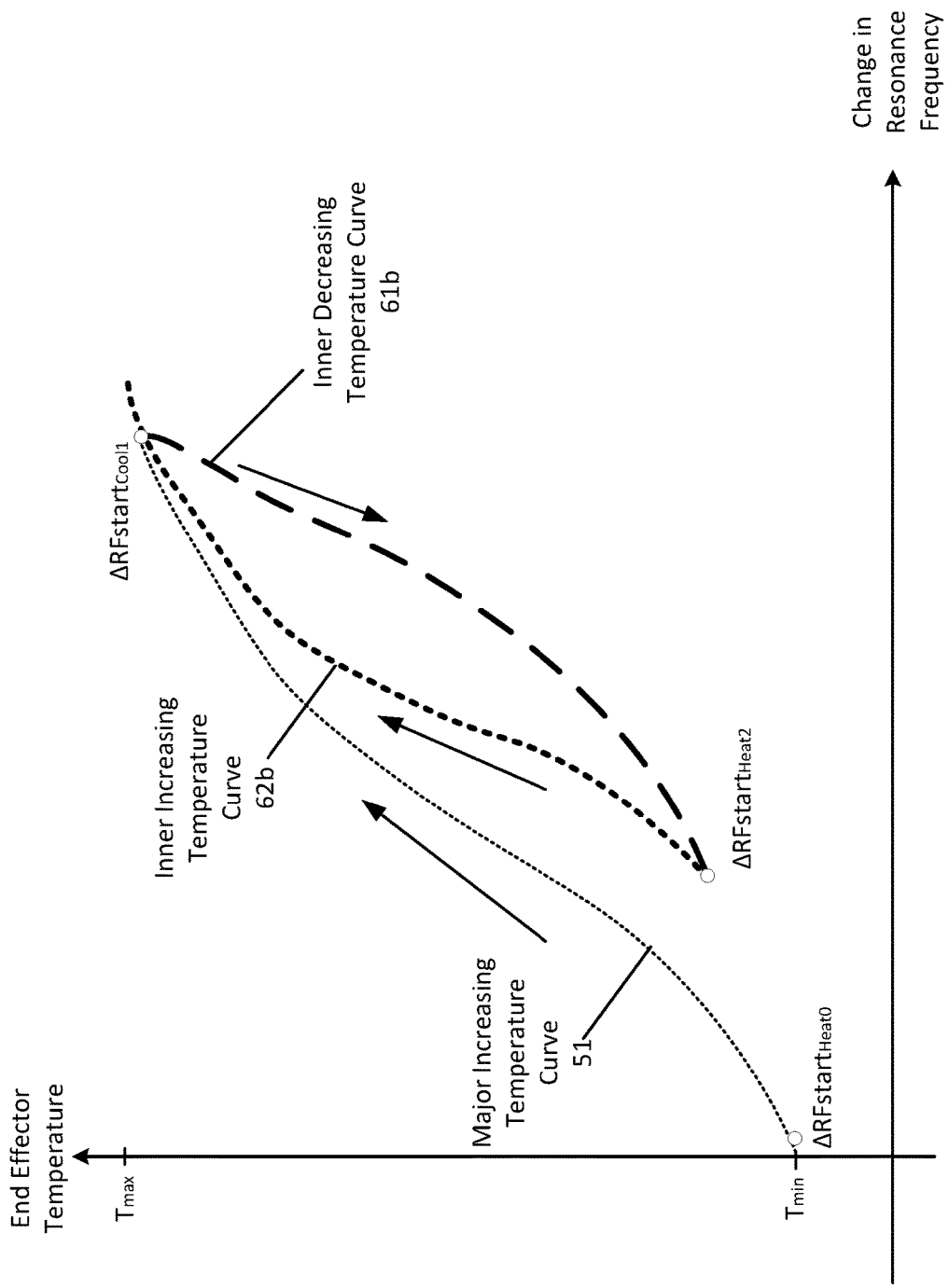
FIG. 9 shows a graphical representation of determined temperatures while the ultrasonic instrument is used according to one aspect.

FIG. 9 shows a graphical representation of determined temperatures while the ultrasonic instrument is used according to one aspect. Specifically, this figure shows the temperature behavior of the ultrasonic instrument according to changes in resonance frequency the end effector, while it is in use. In one aspect, the temperatures of the illustrated curves may be determined (e.g., in real-time) using the hysteresis model according to respective changes in resonance frequency.

At $\Delta RFstart_{Heat0}$ the temperature of the end effector begins to heat above $T_{min}$, which may be the result of the ultrasonic instrument entering the high-power state. The temperature of the end effector follows the major increasing temperature curve 51, which may be due to increasing changes in resonance frequency. At $\Delta RFstart_{Cool1}$ the temperature of the end effector begins to cool. In particular, at this point the change in resonance frequency may begin to decrease (e.g., a first negative value), which may be due to the ultrasonic instrument entering the low-power state. In one aspect, the inner decreasing temperature curve 61b as the ultrasonic instrument cools from $\Delta RFstart_{Cool1}$. At $\Delta RFstart_{Heat2}$, the temperature of the end effector may begin to heat, which may be due to the ultrasonic instrument re-entering the high-power state. The temperature of the ultrasonic instrument may follow the inner increasing temperature curve 62b associated with $\Delta RFstart_{Heat2}$, as the temperature of the end effector reaches $T_{max}$.

Figure 10:
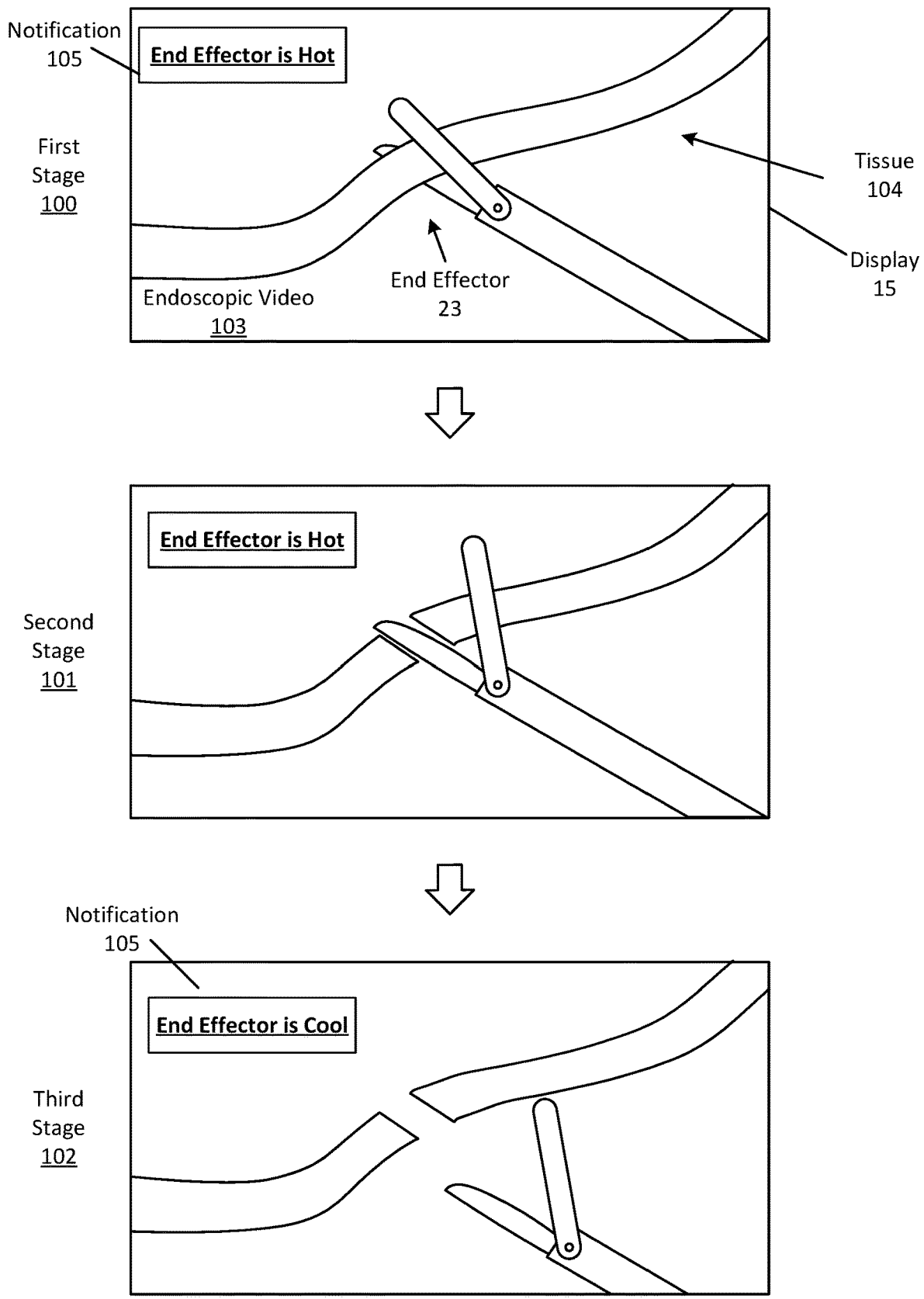
FIG. 10 show several stages of a display of the surgical system that is showing actions performed by an end effector of the ultrasonic instrument and shows a notification based on the determined temperature of the end effector.

FIG. 10 show several stages of a display of the surgical system that is showing actions performed by an end effector of the ultrasonic instrument and shows a notification based on the determined temperature of the end effector. Specifically, each of the three stages 100-102 is showing the display 15 of the surgical system 1, which is displaying endoscopic video 103. The video may be provided by one or more endoscopic cameras of the system, shows a surgical site within a patient to which a surgical procedure is being performed. In particular, the video 103 shows tissue 104 (e.g., a blood vessel) that is being manipulated by the end effector 23. In another aspect, the display may show other content, such as other video content and/or a graphical user interface (GUI) of the surgical system that is displaying one or more UI items.

The first stage 100 shows that the end effector 23 is grasping (a portion of) the tissue 104. In particular, the grasper has been positioned such that the tissue is disposed between the hinged arm 31 and the blade 30, and the hinged arm has been moved towards the blade 30 such that the tissue is sandwiched between (e.g., in contact with) both arms. In addition, the ultrasonic instrument of the end effector is being used to perform ultrasonic instrument operations upon the tissue. Specifically, the ultrasonic instrument may be in the high-power state in which the end effector is vibrating while in contact with the tissue 104, thereby producing frictional heat in order to cut and seal the tissue.

This first stage also shows a notification 105 that is being output by the surgical system. Specifically, the notification is being displayed, as a GUI item that is overlaid on top of the endoscopic video 103. In particular, the notification includes text of "End Effector is Hot" in order to alert the operator of the temperature state of the end effector. In another aspect, the notification may be present separately from (e.g., other) video and/or images that are displayed on the display 15. In one aspect, the notification may be output based on the controller determining the temperature of the end effector, as described herein. In some aspects, the notification may be presented upon the temperature of the end effector reaching a threshold.

The second stage 101 shows the result of cutting and sealing the tissue with the end effector. As shown, the tissue has been cut into two pieces by the end effector and has also been cauterized. In addition, the grasper is now in the open position (with the hinged arm 31 being moved away from the blade 30). With the tissue being cut, the operator may no longer need to heat the end effector, and therefore the instrument may switch from the high-power state to the low-power state in order to enter a cooling cycle, as described herein. Thus, in this stage the ultrasonic instrument may be provided current (e.g., by the generator 25) that is below a current threshold at which the instrument causes the blade of the end effector to produce (e.g., frictional) heat (e.g., when in contact with an object, such as tissue). In addition, at this stage the (controller 40 of the) surgical system may be configured to estimate the temperature of the end effector based on changes in the resonance frequency, which at this stage may be decreasing, as described herein.

Specifically, since at this stage the end effector has just entered the cooling cycle, the blade may still be hot (or above a temperature threshold). In particular, the controller may be configured to compare a current temperature of the end effector to the temperature threshold. At this stage, the current temperature is above the threshold, and as a result, the notification 105 that is displayed on the display continues to read "End Effector is Hot", in order to alert the operator that the end effector continuous to have residual heat from the heating cycle.

The third stage 102 shows that the notification 105 has changed from "End Effector is Hot" to "End Effector is Cool". Specifically, this stage shows that after a period of time, the residual heat within the end effector has subsided such that its determined temperature (e.g., based on changes in resonance frequency) has dropped below the temperature threshold, as described herein.

As described herein, the surgical system 1 may be configured to estimate a temperature of the end effector while the ultrasonic instrument is in either the high-power state (e.g., being actively used by an operator to cut and cauterize tissue) or the low-power state (e.g., the state where the ultrasonic instrument cools down after the operator has used the instrument to cut and cauterize tissue). In one aspect, the operator may switch between these two states one or more times during a surgical procedure. As soon as an operator switches from applying high power through the generator to the low-power state, the end effector may rapidly start cooling down (e.g., to body temperature, such as ~37° C.). If the operator were to switch back to the high-power state, the end effector will start heating up again. In some cases, the end effector may take some time to heat back up to a desired temperature. In one aspect, the controller may be configured to maintain a desired temperature of the end effector in order to reduce the amount of time between the cooling and heating cycles.

As described herein, the display 15 is arranged to present the endoscopic video 103 and the notification 105. In one embodiment, the generator's display 24 may display the video and/or notification. For example, the display 24 may display the endoscopic video and the notification, or may display the notification, while the display 15 of the system presents the endoscopic video.

Figure 11:
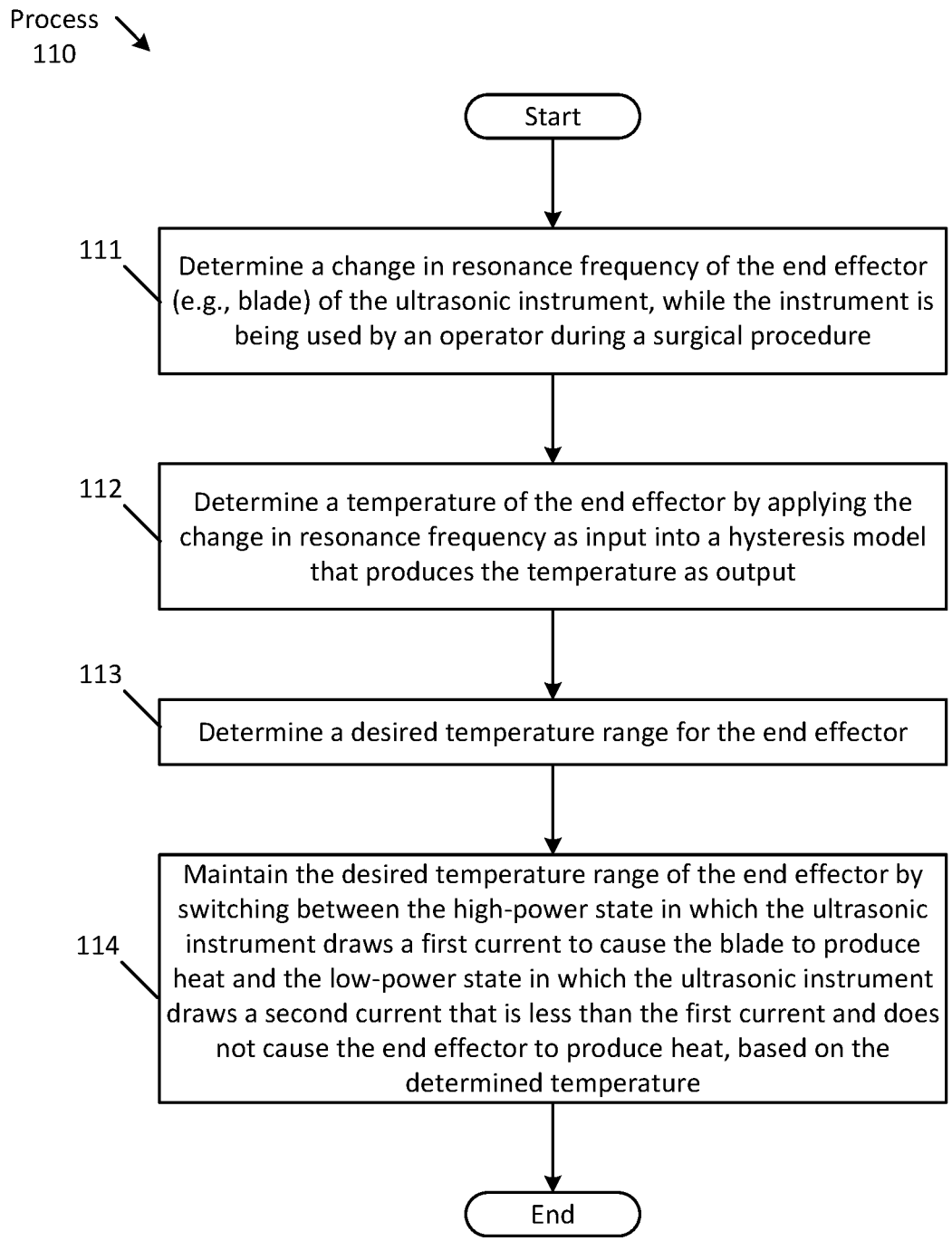
FIG. 11 is a flowchart of a process for maintaining a desired temperature of the ultrasonic instrument.

FIG. 11 is a flowchart of a process 110 for maintaining a desired temperature of the (e.g., end effector of the) ultrasonic instrument. In particular, the controller maintains the desired temperature by controlling whether the ultrasonic instrument is in the high or low-power state based on one or more changes in resonance frequency of the end effector. In one aspect, the process may be performed automatically (e.g., without user interference), such that the temperature of the end effector is maintained at (or within) a desired temperature range.

The process 110 begins by the controller 40 determining a change in resonance frequency of the end effector (e.g., blade) of the ultrasonic instrument, while the instrument is being used by an operator during a surgical procedure (at block 111). Specifically, the change in resonance frequency may be determined while the ultrasonic instrument is operating in one of the power states described herein. The controller determines a temperature of the end effector by applying the change in resonance frequency as input into a hysteresis model (e.g., model 45) that produces the temperature as output (at block 112). The controller determines a desired temperature range for the end effector (at block 113). In one aspect, the desired temperature range may include one or more temperature values. For example, the temperature range may include one or more temperature values (e.g., between 300° C. and 315° C.). In another aspect, the temperature range may include all temperature values above a particular temperature value. In which case, the temperature range may be a single temperature value (e.g., 300° C.), above which the end effector is set operate. In which case, the desired temperature range may be a particular user-desired (or user-defined) temperature. For example, the operator may desire a certain temperature to perform a surgical task upon a particular piece of tissue. In another aspect, the desired temperature range may be determined from user input via an input device (e.g., via a touch-sensitive display screen of an electronic device) that is communicatively coupled to the surgical system. In another aspect, the desired temperature range may be determined based on tissue of the patient to which the end effector of the ultrasonic instrument is going to perform a surgical task. For example, the controller may receive endoscopic video of a surgical site, and perform an image recognition algorithm upon the video to identify a piece of tissue in the site upon which a surgical task (e.g., cutting, etc.) is to be performed by the ultrasonic instrument. The controller may determine the desired temperature based on the piece of identified tissue. For example, fatty tissue may have a higher temperature range than thinner tissue, due to the amount of extra heat that may be required to cut and cauterize the fatty tissue.

The controller 40 maintains the desired temperature range of the end effector by switching between the high-power state in which the ultrasonic instrument draws a first current to cause the end effector to produce heat and the low-power state in which the ultrasonic instrument draws a second current that is less than the first current and does not cause the end effector to produce heat, based on the determined temperature (at block 114). Specifically, the controller maintains the temperature of the end effector to be within the desired range. This may be done by determining whether the determined temperature of the end effector is within (e.g., including boundary values) the temperature range. In response to determining that the determined temperature greater than the desired temperature range (or value), the ultrasonic instrument is configured to operate in the low-power state (e.g., for the end effector to not produce heat, since it is hot enough). Conversely, in response to the controller determining that the desired temperature is less than the desired temperature range, the ultrasonic instrument is configured to operate in the high-power state (e.g., to produce heat).

In one aspect, the temperature of the end effector may be maintained at (or within) the desired temperature range while the ultrasonic instrument is being used by the operator. Specifically, the system may maintain the temperature while the operator is performing surgical tasks with the instrument, such as cutting and/or cauterizing tissue.

In one aspect, the controller may continuously perform at least some of these operations in order to maintain the desired temperature range of the end effector (e.g., while the ultrasonic instrument is being used by an operator). Thus, the operations performed by the controller functionally create a "software sensor", where the state of the ultrasonic instrument is controlled based on changes in resonance frequency, rather than using temperature sensor data from a temperature sensor. As a result, the desired temperature range is determined and maintained without (e.g., the surgical system) using (and/or having) a temperature sensor.

As described herein, the ultrasonic instrument 20 may be a laparoscopic instrument that is held and manipulated by an operator. In another embodiment, the instrument may be a part of a surgical robotic arm. For example, the ultrasonic instrument may be coupled to a distal end of a robotic arm (e.g., arm 4 in FIG. 1), where movement and operation of the ultrasonic instrument may be performed via one or more user controls (e.g., UIDs, foot pedals, etc.) that are coupled to the surgical system. In some embodiments, the ultrasonic instrument may be coupled to an arm, and controlled by the generator based on user input. For example, the generator may control the rotational position of the hinged arm 31, so as to open or close the grasper 23 based on user input, via one or more user input devices, such as the UID 14, that are communicatively coupled to the generator, as described herein. In another aspect, the generator may adjust a spatial position (e.g., in space) of the end effector based on the user input (e.g., based on a position of the UID). In another aspect, the spatial position and/or the rotational position of the hinged arm may be controlled by the controller 40 (e.g., based on user input received by the controller).

Figure 12:
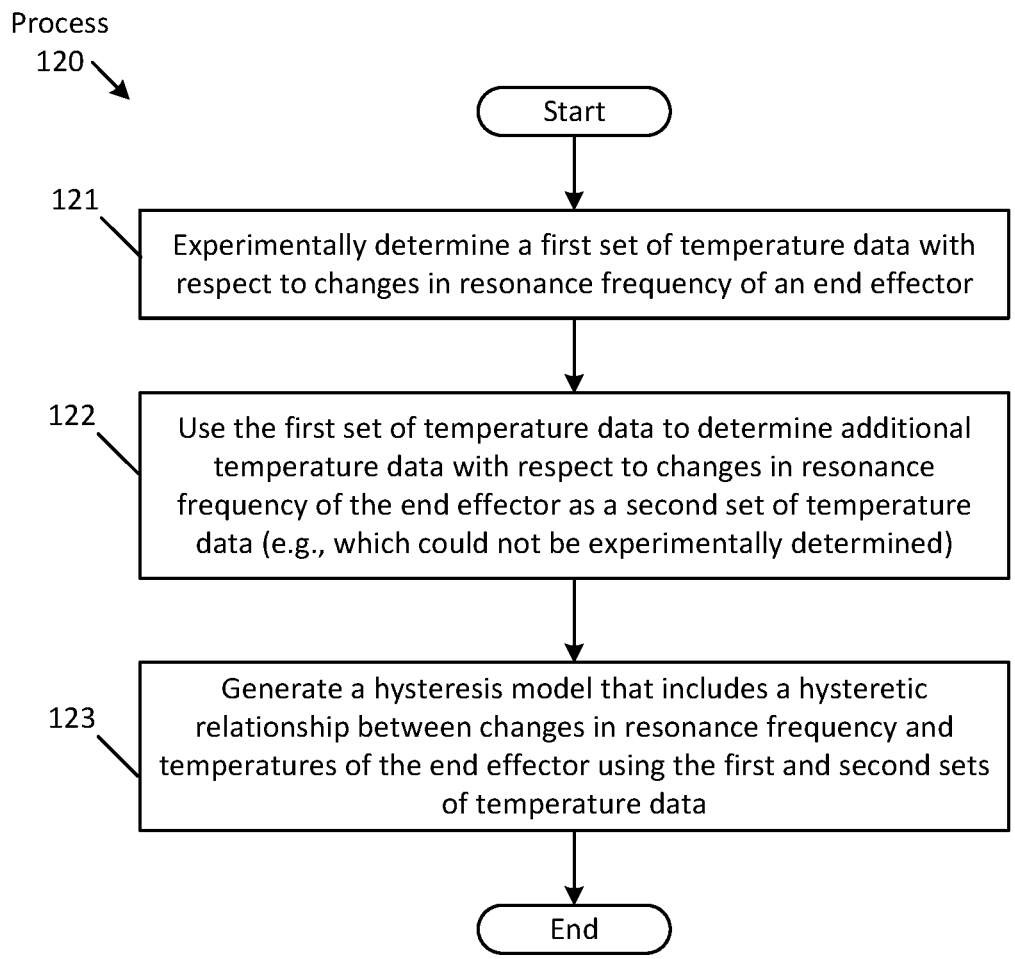
FIG. 12 is a flowchart of a process for creating a hysteresis model that defines a hysteresis relationship between temperature and changes in resonance frequency.

FIG. 12 is a flowchart of a process 120 for creating a hysteresis model (e.g., model 45 in FIG. 4) that defines a hysteresis relationship between temperature and changes in resonance frequency of an end effector of an ultrasonic instrument. In one aspect, this process (or at least some of the operations of this process) may be performed in a controlled environment. In which case, the model may be predefined such that it is created and a part of the surgical system for use during surgical procedures.

The process 120 begins by experimentally determining a first set of temperature data with respect to changes in resonance frequency of an end effector (at block 121). Specifically, the experimental data is determined for an end effector of an ultrasonic instrument that is configured to operate in either 1) a high-power state in which the instrument draws power for the end effector to produce heat or 2) a low-power state in which the instrument draws less power that does not cause the end effector to produce heat, as described herein. In one aspect, the temperature data may include temperature values of the end effector with respect to (e.g., changes in) resonance frequency, while the end effector is heated and cooled. For example, when heating (and cooling) the end effector, the system may monitor the temperature of the end effector (e.g., using a temperature sensor) at one or more discretized levels of (changes in) resonance frequency of the end effector, which may be determined based on data from the generator 25. In one aspect, the controller may obtain the major hysteresis loop (e.g., loop 50 in FIG. 5) by heating the end effector to a maximum temperature (e.g., $T_{max}$) and then cooling it to a minimum temperature (e.g., $T_{min}$). In some aspects, the controller may also obtain one or more inner decreasing (and/or increasing) temperature curves, each of which start at particular changes in resonance frequencies.

The controller uses the first set of temperature data to determine additional temperature data with respect to changes in resonance frequency of the end effector as a second set of temperature data (at block 122). In particular, the controller is determining (or identifying) missing sampling points based on the available experimental data that could not or was not experimentally determined. In some aspects, the controller may use one or more methods to determine this additional temperature data. For example, the controller may be configured to perform interpolation between at least two adjacent temperature curves, which were experimentally determined. For example, two data points from the two closest cooling (decreasing) curves that are available in the experimental data (e.g., curves with the closets frequency change at the beginning of the cooling cycle, from $T_{max}$) may be used. In particular, the controller may denote frequency change at the start of the cooling for each of the neighboring curves by $\Delta RFstart_1$ and $\Delta RFstart_2$, where the frequency change for the cooling curve that is to be interpolated may start at $\Delta RFstart_x$, such that $\Delta RFstart_2 < \Delta RFstart_x < \Delta RFstart_2$. Then, for each discrete level of the change in resonance frequency along the cooling curves, $F_1$ and $F_2$, corresponding blade temperature values of the two curves, $T_1$ and $T_2$, may be obtained from the experimental data. With these temperature values and corresponding changes in resonance frequency, temperature values of the interpolated curve, $T_x$, may be obtained with respect to changes in resonance frequency, $F_x$, using the following equation:

$$T_x = T_2 + \frac{(F_2 - F_x)(T_1 - T_2)}{(F_2 - F_1)}$$

When neighboring curves are present in the experimental data, the interpolation approach may provide sufficient temperature data of the end effector to populated required sampling points in the hysteresis model. In some aspects, however, if there are only a few (e.g., less than a threshold number of curves) curves that are available (e.g., due to minimal experimental data that is obtained) and/or the available experimental data does not span the entire range of possible changes in resonance frequency and end effector blades, the controller may perform a polynomial fit approach to obtain (at least some of) the additional temperature data. This approach will now be described.

First, the controller may fit polynomials/functions on each (or at least some of) the experimentally available curves (e.g., modeling the end effector temperature as a function of change in resonance frequency on the curves. For example, for 1 . . . n curves, each curve may be fit as a second order polynomial, such as $$T_1(\Delta RF) = a_1 \Delta RF^2 + b_1 \Delta RF + c_1$$

. . .

$$T_n(\Delta RF) = a_n \Delta RF^2 + b_n \Delta RF + c_n$$

As a result, temperature is a polynomial function of $\Delta RF$. Hence, $T = p(\Delta RF)$, where p is the second order polynomial with an input of $\Delta RF$. In another aspect, temperature may be another function (e.g., a third order polynomial). In one aspect, each of the curves may be decreasing curves and/or increasing curves, as described herein. In one aspect, each of the coefficients, a, b, and c, may be associated with a certain value of change in resonance frequency at the beginning (starting) of the corresponding curve. Specifically, when the curve is an inner decreasing curve, the coefficients may be tied associated with a value at the beginning of the cooling cycle. In one aspect, the controller may find the fit that best describes the change of one or more coefficients as a function of a corresponding starting change in resonance frequency, which may be shown as:

$$a_1 = x_a \Delta RFstart_1 + y_a$$

. . .

$$a_n = x_n \Delta RFstart_n + y_a$$

$$b_1 = x_a \Delta RFstart_1 + y_b$$

. . .

$$b_n = x_b \Delta RFstart_n + y_b$$

$$c_1 = x_c \Delta RFstart_1 + y_c$$

. . .

$$c_n = x_c \Delta RFstart_n + y_c;$$

Hence, $$a = p_a(\Delta RFstart) = x_a \Delta RFstart + y_a$$

$$b = p_b(\Delta RFstart) = x_b \Delta RFstart + y_b$$

$$c = p_n(\Delta RFstart) = x_c \Delta RFstart + y_c.$$

In one aspect, once these correlations are identified based on the experimentally available data, the controller uses the correlations to generate further data to complete missing sampling points for the model. For sampling points on a specific cooling curve, with starting change in resonance frequency $\Delta RFstart_x$ coefficients may be computed that are associated with the fit of the specific cooling curve, as $$a_x = p_a(\Delta RFstart_x)$$

$$b_x = p_b(\Delta RFstart_x)$$

$$x_x = p_c(\Delta RFstart_x)$$

The controller may use the fit function to compute the end effector temperature at each discretized value of change in resonance frequency along the cooling curve, as $$T(\Delta RF_i) = p(\Delta RFi) = a_x \Delta RF_i^2 + b_x \Delta RF_i + c_x$$

As described herein, the controller may interpolate temperature values and/or compute temperature values using a polynomial fitting approach along cooling curves. In another aspect, the controller may perform either (or both) of these approaches for determining temperature data of heating (or increasing) curves, which may start along the major decreasing temperature curve of the major hysteresis loop.

Returning to the process 120, the controller generates a hysteresis model that includes a hysteretic relationship between changes in resonance frequency and temperatures of the end effector using the first and second sets of temperature data (at block 123). In particular, the controller determines turn on/off thresholds of each hysteron ($\alpha$, $\beta$) and a weight factor, $\mu$, for each hysteron. For instance, the controller discretizes an input domain (e.g., change in resonance frequency), where each hysteron is defined by one or more discrete levels. The controller determines the weight of each hysteron by forming a temperature table (e.g., a lookup table) using temperature data (e.g., the first and second sets of temperature data). To do this, the controller may perform the following sequence, 1) increase the change in resonance frequency to $\alpha$, 2) the controller may tabulate the corresponding end effector temperature, 3) the controller may decrease the change in resonance frequency by one level (e.g., by a threshold amount), 4) again, the controller may tabulate the corresponding end effector temperature, and 5) the controller may continue to keep decreasing the change in resonance frequency and tabulating the corresponding temperature value until the change in resonance frequency is zero. In one aspect, the controller may repeat steps 1) through 5) until α reaches a maximum possible resonance frequency change.

In one aspect, the resulting temperature table is used to compute the weight factor of each hysteron based on the individual contribution of each cell to the output (e.g., end effector temperature). Defining the blade temperature corresponding to αi and βi—tabulated in the $i^{th}$ row and $j^{th}$ column of the formed table—as f(ij), then the corresponding weight factors would be computed based on the following $$\mu(i,j) = f(i+1, j+1) + f(i,j) - f(i+1,j) - f(i,j+1)$$

In one aspect, diagonal elements of the table were i=j=k, the weight factor would be computed based on $$\mu(k,k) = f(k+1, k+1) - f(k+1, k)$$

In some aspects, the determined weight factors may be stored in a table, where each cell in the table is a weight, μ, of an individual hysteron that has a distinct turn on α and turn off level, β. As a result, when the hysteresis model is used to determine the temperature of the end effector, the weight factors may be determined by performing a table lookup into the table, according to one or more hysterons of the model.

In one aspect, a method performed by a surgical system that includes an ultrasonic instrument with an end effector, the method comprising experimentally determining a first set of temperature data with respect to changes in resonance frequency of the end effector of the ultrasonic instrument that is configured to operate in either 1) a high-power state in which the ultrasonic instrument draws power for the end effector to produce beat or 2) a low-power state in which the ultrasonic instrument draws less power that does not cause the end effector to produce heat; using the first set of temperature data to determine additional temperature data with respect to changes in resonance frequency of the end effector as a second set of temperature data; and generating a hysteresis model that includes a hysteretic relationship between changes in resonance frequency and temperatures of the end effector using the first and second sets of temperature data.

As previously explained, an aspect of the disclosure may be a non-transitory machine-readable medium (such as microelectronic memory) having stored thereon instructions, which program one or more data processing components (generically referred to here as a "processor") to (automatically) perform ultrasonic instrument operations and/or temperature estimation and notification operations, as described herein. In other aspects, some of these operations might be performed by specific hardware components that contain hardwired logic. Those operations might alternatively be performed by any combination of programmed data processing components and fixed hardwired circuit components.

While certain aspects have been described and shown in the accompanying drawings, it is to be understood that such aspects are merely illustrative of and not restrictive on the broad disclosure, and that the disclosure is not limited to the specific constructions and arrangements shown and described, since various other modifications may occur to those of ordinary skill in the art. The description is thus to be regarded as illustrative instead of limiting.

In some aspects, this disclosure may include the language, for example, "at least one of [element A] and [element B]." This language may refer to one or more of the elements. For example, "at least one of A and B" may refer to "A," "B," or "A and B." Specifically, "at least one of A and B" may refer to "at least one of A and at least one of B," or "at least of either A or B." In some aspects, this disclosure may include the language, for example, "[element A], [element B], and/or [element C]." This language may refer to either of the elements or any combination thereof. For instance, "A, B, and/or C" may refer to "A," "B," "C," "A and B," "A and C," "B and C," or "A, B, and C."

What is claimed is:

1. A method performed by a surgical system that includes an ultrasonic instrument with an end effector, the method comprising:
    determining a change in resonance frequency of the end effector while the ultrasonic instrument is either in 1) a high-power state in which the ultrasonic instrument draws a first current to cause the end effector to produce heat or 2) a low-power state in which the ultrasonic instrument draws a second current, which is less than the first current that does not cause the end effector to produce heat;
    determining a temperature of the end effector by applying the change in resonance frequency to a hysteresis model that includes a hysteretic relationship between changes in resonance frequency of the end effector and corresponding temperatures of the end effector; and
    outputting a notification based on the temperature.

2. The method of claim 1, wherein determining the temperature of the end effector comprises:
    determining the temperature to be a first temperature when the change in resonance frequency is a positive value; and
    determining the temperature to be a second temperature that is less than the first temperature when the change in resonance frequency is a negative value.

3. The method of claim 1, wherein the hysteresis model comprises a hysteresis loop that includes a first temperature curve that has a first plurality of temperatures with respect to a plurality of changes in resonance frequency, and a second temperature curve that has a second plurality of temperatures with respect to the plurality of changes in resonance frequency that are different than the first plurality of temperatures.

4. The method of claim 3, wherein temperatures of the first plurality of temperatures increase with respect to increasing changes in resonance frequency, and temperatures of the second plurality of temperatures decrease with respect to decreasing changes in resonance frequency.

5. The method of claim 3, wherein the hysteresis model further comprises a set of inner decreasing temperature curves that are contained within the hysteresis loop, each having a set of temperatures with respect to a set of changes in resonance frequency,
    wherein determining the temperature of the end effector comprises:
        selecting an inner decreasing temperature curve from the set of inner decreasing temperature curves based on the change in resonance frequency being associated with a respective set of changes in resonance frequency; and
        identifying the temperature from a respective set of temperatures of the inner decreasing temperature curve that corresponds to the change in resonance frequency.

6. The method of claim 5, wherein the change in resonance frequency is a negative change in resonance frequency, the set of temperatures is a first set of temperatures, and the set of changes in resonance frequency is a first set of changes in resonance frequency, wherein the hysteresis model further comprises a set of inner increasing temperature curves that are contained within the hysteresis loop, each having a second set of temperatures with respect to a second set of changes in resonance frequency, wherein the method further comprises:
   determining a positive change in resonance frequency;
   selecting an inner increasing temperature curve based on the positive change in resonance frequency being associated with a respective second set of changes in resonance frequency; and
   identifying a higher temperature than the temperature that is along the inner increasing temperature curve that corresponds to the positive change in resonance frequency.

7. The method of claim 3, wherein each change in resonance frequency of the plurality of changes is associated with a respective temperature of the second plurality of temperatures and another respective temperature of the first plurality of temperatures that is greater than the respective temperature of the second plurality of temperatures.

8. The method of claim 7, wherein determining the temperature comprises:
   using the first temperature curve to identify the temperature that corresponds to the change in resonance frequency, while the ultrasonic instrument is in the high-power state; and
   using the second temperature curve to identify the temperature that corresponds to the change in resonance frequency, while the ultrasonic instrument is in the low-power state.

9. The method of claim 1 further comprising:
   determining a desired temperature range for the end effector; and
   maintaining the temperature of the end effector within the desired temperature range by controlling whether the ultrasonic instrument is in the high-power state or the low-power state based on one or more changes in resonance frequency of the end effector.

10. The method of claim 1, wherein outputting the notification comprises at least one of:
    displaying the temperature on a display of the surgical system; and
    driving a speaker with an audio signal that includes an audible alert that relates to the temperature.

11. A surgical system comprising:
    an ultrasonic instrument with an end effector;
    a processor; and
    memory having instructions which when executed by the processor causes the surgical system to:
    determine a change in resonance frequency of the end effector while the ultrasonic instrument is either in 1) a heating cycle or 2) a cooling cycle;
    determine a temperature of the end effector by applying the change in resonance frequency to a hysteresis model that includes a hysteretic relationship between changes in resonance frequency of the end effector and corresponding temperatures of the end effector; and
    output a notification based on the temperature.

12. The surgical system of claim 11, wherein the instructions to determine the temperature of the end effector comprises instructions to:
    determine the temperature to be a first temperature when the change in resonance frequency is a positive value; and
    determine the temperature to be a second temperature that is less than the first temperature when the change in resonance frequency is a negative value.

13. The surgical system of claim 11, wherein the hysteresis model comprises a hysteresis loop that includes a first temperature curve that has a first plurality of temperatures with respect to a plurality of changes in resonance frequency, and a second temperature curve that has a second plurality of temperatures with respect to the plurality of changes in resonance frequency that are different than the first plurality of temperatures.

14. The surgical system of claim 13, wherein temperatures of the first plurality of temperatures increase with respect to increasing changes in resonance frequency, and temperatures of the second plurality of temperatures decrease with respect to decreasing changes in resonance frequency.

15. The surgical system of claim 13, wherein the instructions to determine the temperature comprises instructions to:
    use the first temperature curve to identify the temperature that corresponds to the change in resonance frequency, while the ultrasonic instrument is in the heating cycle; and
    use the second temperature curve to identify the temperature that corresponds to the change in resonance frequency, while the ultrasonic instrument is in the cooling cycle.

16. The surgical system of claim 11, wherein the end effector comprises a blade that is arranged to vibrate along a longitudinal axis of the end effector, wherein the blade vibrates 1) over a first excursion while the ultrasonic instrument is in the heating cycle and 2) over a second excursion that is less than the first excursion while the ultrasonic instrument is in the cooling cycle.

17. The surgical system of claim 11, wherein the memory has further instructions to:
    determine a desired temperature range for the end effector; and
    maintain the temperature of the end effector within the desired temperature range by controlling whether the ultrasonic instrument is in the heating cycle or the cooling cycle based on one or more changes in resonance frequency of the end effector.

18. The surgical system of claim 11, wherein the instructions to output the notification comprises at least one of:
    display the temperature on a display of the surgical system; and
    drive a speaker with an audio signal that includes an audible alert that relates to the temperature.

19. The surgical system of claim 11, wherein the temperature of the end effector is determined using one or more signal processing operations without using temperature data from a temperature sensor.

20. A method performed by a surgical system that includes an ultrasonic instrument with a blade, the method comprising:
    determining a change in resonance frequency of the blade;
    determining a temperature of the blade by applying the change in resonance frequency as input into a hysteresis model that produces the temperature as output; and
    maintaining a desired temperature range of the blade by switching between a high-power state in which the ultrasonic instrument draws a first current to cause the blade to produce heat and a low-power state in which the ultrasonic instrument draws a second current that is less than the first current and does not cause the blade to produce heat, based on the determined temperature.

\* \* \* \* \*